US011871995B2

(12) United States Patent
Kosior et al.

(10) Patent No.: US 11,871,995 B2
(45) Date of Patent: *Jan. 16, 2024

(54) PATIENT-SPECIFIC MODELING OF HEMODYNAMIC PARAMETERS IN CORONARY ARTERIES

(71) Applicant: HEMOLENS DIAGNOSTICS SP. Z.O.O., Wroclaw (PL)

(72) Inventors: Andrzej Kosior, Wroclaw (PL); Kryspin Mirota, Wroclaw (PL); Wojciech Tarnawski, Wroclaw (PL)

(73) Assignee: Hemolens Diagnostics Sp. z o.o., Wroclaw (PL)

( * ) Notice: Subject to any disclaimer, the term of this patent is extended or adjusted under 35 U.S.C. 154(b) by 1316 days.

This patent is subject to a terminal disclaimer.

(21) Appl. No.: 16/217,328

(22) Filed: Dec. 12, 2018

(65) Prior Publication Data
US 2019/0183579 A1    Jun. 20, 2019

Related U.S. Application Data

(60) Provisional application No. 62/599,930, filed on Dec. 18, 2017.

(51) Int. Cl.
*A61B 34/10* (2016.01)
*A61B 6/03* (2006.01)
(Continued)

(52) U.S. Cl.
CPC .......... *A61B 34/10* (2016.02); *A61B 5/0044* (2013.01); *A61B 5/021* (2013.01); *A61B 5/02007* (2013.01); *A61B 5/02028* (2013.01); *A61B 5/0263* (2013.01); *A61B 6/032* (2013.01); *A61B 6/504* (2013.01); *A61B 6/507* (2013.01); *A61B 6/5217* (2013.01); *A61B 6/5247* (2013.01); *G16H 10/60* (2018.01); *G16H 30/40* (2018.01); *G16H 50/50* (2018.01); *A61B 2034/105* (2016.02); *A61B 2034/108* (2016.02); *A61B 2505/05* (2013.01); *A61B 2576/023* (2013.01)

(58) Field of Classification Search
None
See application file for complete search history.

(56) References Cited

U.S. PATENT DOCUMENTS 6,236,878 B1    5/2001   Taylor et al.
7,860,290 B2   12/2010   Gulsun et al.
(Continued)

OTHER PUBLICATIONS

Kim et al. (Annals of Biomedical Engineering (2010) vol. 38:3195-3209).*
(Continued)

*Primary Examiner* — Lori A. Clow
(74) *Attorney, Agent, or Firm* — DLA Piper LLP (US)

(57) ABSTRACT

Systems, methods, and computer-readable media are disclosed for patient-specific modeling of hemodynamic parameters in coronary arteries. Example methods may include performing computational fluid dynamics simulations using a patient-specific coronary artery anatomical model derived from medical imaging data and patient-specific boundary conditions derived from a continuously recorded blood pressure waveform to determine patient-specific hemodynamic parameters in a patient's coronary arteries.

20 Claims, 25 Drawing Sheets

(51) Int. Cl.
    *A61B 6/00*     (2006.01)
    *A61B 5/021*    (2006.01)
    *G16H 10/60*    (2018.01)
    *G16H 50/50*    (2018.01)
    *G16H 30/40*    (2018.01)
    *A61B 5/026*    (2006.01)
    *A61B 5/02*     (2006.01)
    *A61B 5/00*     (2006.01)

(56) References Cited

U.S. PATENT DOCUMENTS

| | | |
|---|---|---|
| 7,953,266 B2 | 5/2011 | Gulsun et al. |
| 8,311,747 B2 | 11/2012 | Taylor |
| 8,315,812 B2 | 11/2012 | Taylor |
| 8,315,813 B2 | 11/2012 | Taylor et al. |
| 8,315,814 B2 | 11/2012 | Taylor et al. |
| 8,386,188 B2 | 2/2013 | Taylor et al. |
| 8,496,594 B2 | 7/2013 | Taylor et al. |
| 8,548,778 B1 | 10/2013 | Hart et al. |
| 8,594,950 B2 | 11/2013 | Taylor |
| 8,706,457 B2 | 4/2014 | Hart et al. |
| 8,734,356 B2 | 5/2014 | Taylor |
| 8,768,669 B1 | 7/2014 | Hart et al. |
| 8,812,246 B2 | 8/2014 | Taylor |
| 8,824,752 B1 | 9/2014 | Fonte et al. |
| 8,831,314 B1 | 9/2014 | Fonte et al. |
| 8,831,315 B1 | 9/2014 | Fonte et al. |
| 8,837,860 B1 | 9/2014 | Grady et al. |
| 8,861,820 B2 | 10/2014 | Fonte et al. |
| 8,914,264 B1 | 12/2014 | Hart et al. |
| 8,917,925 B1 | 12/2014 | Grady et al. |
| 8,958,623 B1 | 2/2015 | Grady et al. |
| 9,002,690 B2 | 4/2015 | Hart et al. |
| 9,008,392 B1 | 4/2015 | Bai et al. |
| 9,008,405 B2 | 4/2015 | Fonte et al. |
| 9,042,613 B2 | 5/2015 | Spilker et al. |
| 9,043,190 B2 | 5/2015 | Grady et al. |
| 9,043,191 B2 | 5/2015 | Grady et al. |
| 9,058,692 B1 | 6/2015 | Grady et al. |
| 9,063,635 B2 | 6/2015 | Hart et al. |
| 9,070,214 B1 | 6/2015 | Grady et al. |
| 9,078,564 B2 | 7/2015 | Taylor |
| 9,081,721 B1 | 7/2015 | Grady et al. |
| 9,081,882 B2 | 7/2015 | Taylor |
| 9,087,147 B1 | 7/2015 | Fonte |
| 9,149,197 B2 | 10/2015 | Taylor |
| 9,152,757 B2 | 10/2015 | Taylor |
| 9,152,761 B2 | 10/2015 | Bhatia et al. |
| 9,153,047 B1 | 10/2015 | Grady et al. |
| 9,155,512 B2 | 10/2015 | Choi et al. |
| 9,159,159 B2 | 10/2015 | Bai et al. |
| 9,189,600 B2 | 11/2015 | Spilker et al. |
| 9,195,800 B2 | 11/2015 | Grady et al. |
| 9,195,801 B1 | 11/2015 | Sankaran et al. |
| 9,202,010 B2 | 12/2015 | Taylor et al. |
| 9,220,418 B2 | 12/2015 | Choi et al. |
| 9,220,419 B2 | 12/2015 | Choi et al. |
| 9,226,672 B2 | 1/2016 | Taylor |
| 9,235,679 B2 | 1/2016 | Taylor |
| 9,239,905 B1 | 1/2016 | Sankaran et al. |
| 9,262,581 B2 | 2/2016 | Kim et al. |
| 9,268,902 B2 | 2/2016 | Taylor et al. |
| 9,271,657 B2 | 3/2016 | Taylor |
| 9,280,639 B2 | 3/2016 | Sankaran et al. |
| 9,292,659 B1 | 3/2016 | Grady et al. |
| 9,304,982 B2 | 4/2016 | Grady et al. |
| 9,330,233 B2 | 5/2016 | Bhatia et al. |
| 9,336,354 B1 | 5/2016 | Sankaran et al. |
| 9,339,200 B2 | 5/2016 | Fonte |
| 9,378,580 B2 | 6/2016 | Grady et al. |
| 9,386,933 B2 | 7/2016 | Grady et al. |
| 9,390,224 B2 | 7/2016 | Choi et al. |
| 9,390,232 B2 | 7/2016 | Taylor et al. |
| 9,424,395 B2 | 8/2016 | Sankaran et al. |
| 9,424,682 B2 | 8/2016 | Bai et al. |
| 9,449,145 B2 | 9/2016 | Sankaran et al. |
| 9,449,146 B2 | 9/2016 | Spilker et al. |
| 9,449,147 B2 | 9/2016 | Taylor |
| 9,501,622 B2 | 11/2016 | Sankaran et al. |
| 9,514,530 B2 | 12/2016 | Grady et al. |
| 9,517,040 B2 | 12/2016 | Hart et al. |
| 9,585,623 B2 | 3/2017 | Fonte et al. |
| 9,589,349 B2 | 3/2017 | Grady et al. |
| 9,594,876 B2 | 3/2017 | Sankaran et al. |
| 9,607,130 B2 | 3/2017 | Grady et al. |
| 9,607,386 B2 | 3/2017 | Grady et al. |
| 9,613,186 B2 | 4/2017 | Fonte |
| 9,649,171 B2 | 5/2017 | Sankaran et al. |
| 9,668,700 B2 | 6/2017 | Taylor |
| 9,672,615 B2 | 6/2017 | Fonte et al. |
| 9,675,301 B2 | 6/2017 | Fonte et al. |
| 9,679,374 B2 | 6/2017 | Choi et al. |
| 9,754,082 B2 | 9/2017 | Taylor et al. |
| 9,770,303 B2 | 9/2017 | Choi et al. |
| 9,773,219 B2 | 9/2017 | Sankaran et al. |
| 9,785,746 B2 | 10/2017 | Fonte et al. |
| 9,785,748 B2 | 10/2017 | Koo et al. |
| 9,801,689 B2 | 10/2017 | Taylor |
| 9,805,168 B2 | 10/2017 | Sankaran et al. |
| 9,805,463 B2 | 10/2017 | Choi et al. |
| 9,805,470 B2 | 10/2017 | Bhatia et al. |
| 9,836,840 B2 | 12/2017 | Fonte et al. |
| 9,839,399 B2 | 12/2017 | Fonte et al. |
| 9,839,483 B2 | 12/2017 | Sankaran et al. |
| 9,855,105 B2 | 1/2018 | Taylor |
| 9,864,840 B2 | 1/2018 | Grady et al. |
| 9,870,634 B2 | 1/2018 | Grady et al. |
| 9,913,616 B2 | 3/2018 | Fonte et al. |
| 9,965,873 B2 | 5/2018 | Grady et al. |
| 9,965,891 B2 | 5/2018 | Grady et al. |
| 9,974,453 B2 | 5/2018 | Fonte et al. |
| 9,974,616 B2 | 5/2018 | Grady et al. |
| 9,993,303 B2 | 6/2018 | Sankaran et al. |
| 10,007,762 B2 | 6/2018 | Grady et al. |
| 10,010,255 B2 | 7/2018 | Fonte et al. |
| 10,049,093 B2 | 8/2018 | Grady et al. |
| 10,080,613 B2 | 9/2018 | Taylor |
| 10,092,247 B2 | 10/2018 | Taylor |
| 10,092,360 B2 | 10/2018 | Taylor |
| 10,096,104 B2 | 10/2018 | Choi et al. |
| 2010/0006776 A1 | 1/2010 | Tanabe et al. |
| 2012/0041739 A1* | 2/2012 | Taylor ............... A61B 6/5205 703/11 |
| 2012/0072190 A1 | 3/2012 | Sharma et al. |
| 2013/0064438 A1 | 3/2013 | Taylor et al. |
| 2014/0073976 A1 | 3/2014 | Fonte et al. |
| 2014/0073977 A1 | 3/2014 | Grady et al. |
| 2014/0148693 A1 | 5/2014 | Taylor |
| 2015/0065847 A1 | 3/2015 | Choi et al. |
| 2015/0065848 A1 | 3/2015 | Choi et al. |
| 2015/0073722 A1 | 3/2015 | Taylor et al. |
| 2015/0150530 A1 | 6/2015 | Taylor et al. |
| 2015/0164451 A1 | 6/2015 | Choi et al. |
| 2015/0201849 A1 | 7/2015 | Taylor |
| 2015/0245775 A1 | 9/2015 | Fonte et al. |
| 2015/0269350 A1 | 9/2015 | Taylor et al. |
| 2015/0269351 A1 | 9/2015 | Taylor et al. |
| 2015/0278976 A1 | 10/2015 | Sankaran et al. |
| 2015/0339459 A1 | 11/2015 | Taylor |
| 2015/0363941 A1 | 12/2015 | Taylor |
| 2016/0038251 A1 | 2/2016 | Grady et al. |
| 2016/0066862 A1 | 3/2016 | Taylor |
| 2016/0073991 A1 | 3/2016 | Taylor |
| 2016/0103816 A1 | 4/2016 | Grady et al. |
| 2016/0113528 A1 | 4/2016 | Taylor |
| 2016/0132657 A1 | 5/2016 | Kim et al. |
| 2016/0175053 A1 | 6/2016 | Sankaran et al. |
| 2016/0203289 A1 | 7/2016 | Grady et al. |
| 2016/0210428 A1 | 7/2016 | Spilker et al. |
| 2016/0220123 A1 | 8/2016 | Grady et al. |
| 2016/0220124 A1 | 8/2016 | Grady et al. |
| 2016/0220193 A1 | 8/2016 | Grady et al. |
| 2016/0224744 A1 | 8/2016 | Grady et al. |

(56) References Cited

U.S. PATENT DOCUMENTS

| | | |
|---|---|---|
| 2016/0224753 A1 | 8/2016 | Grady et al. |
| 2016/0224758 A1 | 8/2016 | Grady et al. |
| 2016/0246939 A1 | 8/2016 | Taylor |
| 2016/0283688 A1 | 9/2016 | Taylor et al. |
| 2016/0283689 A1 | 9/2016 | Grady et al. |
| 2016/0287093 A1 | 10/2016 | Choi et al. |
| 2016/0287338 A1 | 10/2016 | Grady et al. |
| 2016/0292382 A1 | 10/2016 | Grady et al. |
| 2016/0292383 A1 | 10/2016 | Choi et al. |
| 2016/0292384 A1 | 10/2016 | Choi et al. |
| 2016/0296286 A1 | 10/2016 | Bai et al. |
| 2016/0296287 A1 | 10/2016 | Taylor |
| 2016/0296288 A1 | 10/2016 | Sankaran et al. |
| 2016/0306943 A1 | 10/2016 | Choi et al. |
| 2016/0310018 A1 | 10/2016 | Fonte et al. |
| 2016/0317046 A1 | 11/2016 | Fonte et al. |
| 2016/0317114 A1 | 11/2016 | Fonte et al. |
| 2016/0321417 A1 | 11/2016 | Fonte et al. |
| 2016/0342765 A1 | 11/2016 | Sankaran et al. |
| 2016/0346043 A1 | 12/2016 | Jaquet et al. |
| 2016/0364859 A1 | 12/2016 | Taylor |
| 2016/0364860 A1 | 12/2016 | Taylor |
| 2016/0367153 A1 | 12/2016 | Taylor et al. |
| 2016/0371440 A1 | 12/2016 | Taylor et al. |
| 2016/0371456 A1 | 12/2016 | Taylor et al. |
| 2017/0004280 A1 | 1/2017 | Taylor et al. |
| 2017/0007332 A1 | 1/2017 | Spilker et al. |
| 2017/0014033 A1 | 1/2017 | Koo et al. |
| 2017/0014034 A1 | 1/2017 | Koo et al. |
| 2017/0018081 A1 | 1/2017 | Taylor et al. |
| 2017/0027648 A1 | 2/2017 | Hart et al. |
| 2017/0039340 A1 | 2/2017 | Sankaran et al. |
| 2017/0053092 A1 | 2/2017 | Taylor |
| 2017/0076062 A1 | 3/2017 | Choi et al. |
| 2017/0095292 A1 | 4/2017 | Taylor et al. |
| 2017/0132388 A1 | 5/2017 | Grady et al. |
| 2017/0143427 A1 | 5/2017 | Grady et al. |
| 2017/0147780 A1 | 5/2017 | Sankaran et al. |
| 2017/0156679 A1 | 6/2017 | Grady et al. |
| 2017/0161455 A1 | 6/2017 | Grady et al. |
| 2017/0202621 A1 | 7/2017 | Taylor |
| 2017/0220760 A1 | 8/2017 | Fonte |
| 2017/0265831 A1 | 9/2017 | Sankaran et al. |
| 2017/0281011 A1 | 10/2017 | Fonte et al. |
| 2017/0286628 A1 | 10/2017 | Shim |
| 2017/0329930 A1 | 11/2017 | Fonte et al. |
| 2017/0330116 A1 | 11/2017 | Sankaran et al. |
| 2017/0340393 A1 | 11/2017 | Choi et al. |
| 2017/0357773 A1 | 12/2017 | Sankaran et al. |
| 2017/0372096 A1 | 12/2017 | Yousfi et al. |
| 2017/0372476 A1 | 12/2017 | Bhatia et al. |
| 2018/0047304 A1 | 2/2018 | Sankaran et al. |
| 2018/0049705 A1 | 2/2018 | Fonte et al. |
| 2018/0055572 A1 | 3/2018 | Spilker et al. |
| 2018/0068445 A1 | 3/2018 | Fonte et al. |
| 2018/0071027 A1 | 3/2018 | Taylor |
| 2018/0078139 A1 | 3/2018 | Sanders et al. |
| 2018/0085078 A1 | 3/2018 | Sankaran et al. |
| 2018/0089384 A1 | 3/2018 | Grady et al. |
| 2018/0108162 A1 | 4/2018 | Grady et al. |
| 2018/0140258 A1 | 5/2018 | Fonte et al. |
| 2018/0161104 A1 | 6/2018 | Taylor |
| 2018/0182096 A1 | 6/2018 | Grady et al. |
| 2018/0225847 A1 | 8/2018 | Grady et al. |
| 2018/0225863 A1 | 8/2018 | Grady et al. |
| 2018/0235482 A1 | 8/2018 | Fonte et al. |
| 2018/0235707 A1 | 8/2018 | Grady et al. |
| 2018/0243033 A1 | 8/2018 | Tran et al. |
| 2018/0256260 A1 | 9/2018 | Sankaran et al. |
| 2018/0277254 A1 | 9/2018 | Grady et al. |
| 2022/0093266 A1 | 3/2022 | Kosior et al. |

OTHER PUBLICATIONS

Vignon-Clementel et al. Comput. Methods Appl. Mech. Engrg. (2006) vol. 195:3776-3796).*

Sherman T (1981) On connecting large vessels to small—the meaning of murray's law. Journal of General Physiology, 78(4):431-453.

Townsend RHD (2010) Fast calculation of the Lomb-Scargle periodogram using graphics processing units. The Astrophysical Journal, Supplement Series, vol. 191, 247-253.

Dufour, A. et al., Segmenting and tracking fluorescent cells in dynamic 3-D microscopy with coupled active surfaces. IEEE Transactions on Image Processing, 14(9), 1396-1410, 2005.

Dufour, A. et al., J.-C. 3-D active meshes: fast discrete deformable models for cell tracking in 3-D time-lapse microscopy. IEEE Transactions on Image Processing, 20(7), 1925-1937, 2011.

Kass, M. et al., Active contour models. Int. J. of Computer Vision 1(4), 321-331, 1988.

Freund J et al., (2012) Fluid flows and forces in development: functions, features and biophysical principles. Development, 139(7):1229-1245.

Algranati D et al. (2010) Mechanisms of myocardium-coronary vessel interaction. American Journal of Physiology. Heart and Circulatory Physiology, vol. 298, No. 3,H861-H873.

Garcia D et al. (2009) Impairment of coronary flow reserve in aortic stenosis. Journal of Applied Physiology, vol. 106, No. 1, 113-121.

Stergiopulos N et al. (1996) Determinants of stroke volume and systolic and diastolic aortic pressure. American Journal of Physiology, vol. 270, No. 6, Pt.2, H2050-H2059.

Westerhof N et al. (2009) The arterial windkessel. Medical & Biological Engineering & Computing, vol. 47, No. 2, 131-141.

Lankhaar JW et al. (2009) Modeling the instantaneous pressure-volume relation of the left ventricle: a comparison of six models. Annals of biomedical engineering, vol. 37, No. 9, 1710-1726.

Faragallah G et al. (2012) A new control system for left ventricular assist devices based on patient-specific physiological demand. Inverse Problems in Science and Engineering, vol. 20, No. 5, 721-734.

Maceira AM et al. (2006) Reference right ventricular systolic and diastolic function normalized to age, gender and body surface area from steady-state free precession cardiovascular magnetic resonance. European Heart Journal, vol. 27, Issue 23, pp. 2879-2888.

Maceira AM et al. (2006) Normalized left ventricular systolic and diastolic function by steady state free precession cardiovascular magnetic resonance. Journal of Cardiovascular Magnetic Resonance, vol. 8, Issue 3, 417-426.

Tsanas A et al. (2009) The Windkessel model revisited: a qualitative analysis of the circulatory system. Medical Engineering & Physics, vol. 31, Issue 5, 581-588.

Epstein S et al. (2015) Reducing the number of parameters in 1D arterial blood flow modeling: less is more for patient-specific simulations. American Journal of Physiology, Heart and Circulatory Physiology, vol. 309, No. 1, H222-H234.

Kheyfets VO et al. (2016) A zero-dimensional model and protocol for simulating patient-specific pulmonary hemodynamics from limited clinical data. Journal of Biomechanical Engineering, vol. 138, Issue 12,1-8.

Mynard J P et al. (2014) Scalability and in vivo validation of a multiscale numerical model of the left coronary circulation. American Journal of Physiology. Heart and Circulatory Physiology, vol. 306, No. 4, H517-H528.

Westerhof N et al. (2006) Cross-talk between cardiac muscle and coronary vasculature. Physiological Reviews, vol. 86. No. 4, 1263-1308.

Beyar R et al. (1987) Time-dependent coronary blood flow distribution in left ventricular wall. American Journal of Physiology, Heart and Circulatory Physiology, vol. 252, No. 2, Pt.2, H417-H433.

Boileau E et al. (2015) One-Dimensional Modelling of the Coronary Circulation. Application to Noninvasive Quantification of Fractional Flow Reserve (FFR). Computational and Experimental Biomedical Sciences: Methods and Applications, vol. 21, 137-155.

Bruinsma T et al. (1988) Model of the coronary circulation based on pressure dependence of coronary resistance and compliance. Basic Res Cardiol, 83:510-524.

(56) References Cited

OTHER PUBLICATIONS

Burattini R et al. (1985) Identification of canine intramyocardial compliance on the basis of the waterfall model. Annals of Biomedical Engineering, vol. 13, No. 5, 385-404.

Chadwick R S et al. (1990) Phasic regional myocardial inflow and outflow: comparison of theory and experiments. American Journal of Physiology, Heart and Circulatory Physiology, vol. 258, No. 6, H1687-H1698.

Holenstein R et al. (1990) Parametric analysis of flow in the intramyocardial circulation. Annals of Biomedical Engineering, vol. 18, No. 4, 347-365.

Judd R M et al. (1991) Coronary input impedance is constant during systole and diastole. American Journal of Physiology—Heart and Circulatory Physiology, vol. 260, No. 6, H1841-H1851.

Kresh J Y et al. (1990) Model-based analysis of transmural vessel impedance and myocardial circulation dynamics. American Journal of Physiology, Heart and Circulatory Physiology, vol. 258, No. 1, H262-H276.

Lee J et al. (1984) The role of vascular capacitance in the coronary arteries. Circ Res 55:751-762.

Lee J et al. (2012) The multi-scale modelling of coronary blood flow. Annals of Biomedical Engineering, vol. 40, Issue 11, 2399-2413.

Sengupta D et al. (2014) Thrombotic risk stratification using computational modeling in patients with coronary artery aneurysms following Kawasaki disease. Biomechanics and Modeling in Mechanobiology, vol. 13, No. 6, 1261-1276.

Spaan Jae et al. (1981) Diastolic-systolic coronary flow differences are caused by intramyocardial pump action in the anesthetized dog. Circ Res, vol. 49, Issue 3, 584-593.

Young D et al. (1973) Flow characteristics in models of arterial stenoses. II. Unsteady flow, Journal of Biomechanics, vol. 6, No. 5, 547-559.

Young D et al. (1977) Hemodynamics of arterial stenoses at elevated flow rates. Circulation Research, vol. 41, No. 1, 99-107.

"A novel patient-specific model to compute coronary fractional flow reserve", Kwon SS, Chung EC, Park JS, Kim GT, Kim JW, Kim KH, Shin ES, Shim EB. Prog Biophys Mol Biol 2014; 116: 48-55.

"Patient-Specific Coronary Stenoses Can Be Modeled Using a Combination of OCT and Flow Velocities to Accurately Predict Hyperemic Pressure Gradients", Kousera C A et al., IEEE Transactions on Biomedical Engineering, IEEE Service Center, Piscataway, NJ, USA, vol. 61, No. 6, Jun. 1, 2014 (Jun. 1, 2014), pp. 1902-1913, XP011548214, ISSN: 0018-9294, DOI: 10.1109/TBME.2014.2310954.

"Diagnostic Performance of a Novel Method for Fractional Flow Reserve Computed from Noninvasive Computed Tomography Angiography (Novel-Flow Study)", Chung Ju-Hyun et al, American Journal of Cardiology, Cahners Publishing Co., Newton, MA, US, vol. 120, No. 3, May 15, 2017 (May 15, 2017), pp. 362-368, XP085115531, ISSN: 0002-9149, DOI: 10.1016/J.AMJCARD.2017.04.057.

"Expert consensus document on arterial stiffness: methodological issues and clinical applications", Stephane Laurent et al., Eur Heart J. Nov. 2006;27(21):2588-605. doi: 10.1093/eurheartj/ehl254. Epub Sep. 25, 2006.

Diaz et al., "The effects of age on pulse wave velocity in untreated hypertension", J. Clin. Hypertens., 2018, 20:258-265.

Kwon et al., "A novel patient-specific model to compute coronary fractional flow reserve", Progress in Biophysics and Molecular Biology, Sep. 2014, 116:48-55.

Newberry et al., "Testing Foundations of Biological Scaling Theory Using Automated Measurements of Vascular Networks", PLOS Computational Biology, Aug. 2015, 18 pages.

\* cited by examiner

PATIENT-SPECIFIC MODELING OF HEMODYNAMIC PARAMETERS IN CORONARY ARTERIES

CROSS-REFERENCE TO RELATED APPLICATIONS

This application claims the benefit of U.S. Provisional Application No. 62/599,930, filed on Dec. 18, 2017, which is incorporated by reference herein in its entirety.

BACKGROUND

Cardiovascular disease is the leading cause of death for men and women in the United States and accounts for no less than 30% of deaths worldwide. Although medical advances in recent years have provided important improvements in the diagnosis and treatment of cardiac disease, the incidence of premature morbidity and mortality is still large. One reason for this is a lack of accurate estimates of patient-specific parameters that accurately characterize the anatomy, physiology, and hemodynamics of coronary arteries, all of which play an important role in the progression of cardiovascular disease.

Medical imaging based techniques (e.g., computed tomography angiography) are typically used in clinical practice for characterizing the severity of stenosis in the coronary arteries. However, such techniques only provide an anatomical assessment, which is often inadequate for clinical decision making. In particular, anatomical assessment of the severity of coronary artery stenosis often leads to overestimation or underestimation, both of which are undesirable. Overestimation of stenosis severity can lead to unnecessary intervention and subsequent risk of restenosis, while underestimation will likely lead to non-treatment. An accurate functional assessment may require measurements of pressure and/or flow, which are determined invasively.

Several computational fluid dynamics (CFD) based techniques for functional assessment of coronary artery disease have been developed. However, they are typically based on simplified geometries of the coronary arteries, with generic boundary conditions derived from population-wide data. This makes such techniques unsuitable for a comprehensive patient-specific assessment of a coronary artery disease, such as an assessment of stenosis severity in the case of coronary artery stenosis.

BRIEF DESCRIPTION OF THE DRAWINGS

The detailed description is set forth with reference to the accompanying drawings. The drawings are provided for purposes of illustration only and merely depict example embodiments of the disclosure. The drawings are provided to facilitate understanding of the disclosure and shall not be deemed to limit the breadth, scope, or applicability of the disclosure. In the drawings, the left-most digit(s) of a reference numeral may identify the drawing in which the reference numeral first appears. The use of the same reference numerals indicates similar, but not necessarily the same or identical components. However, different reference numerals may be used to identify similar components as well. Various embodiments may utilize elements or components other than those illustrated in the drawings, and some elements and/or components may not be present in various embodiments. The use of singular terminology to describe a component or element may, depending on the context, encompass a plural number of such components or elements and vice versa.

DETAILED DESCRIPTION

Figure 1:
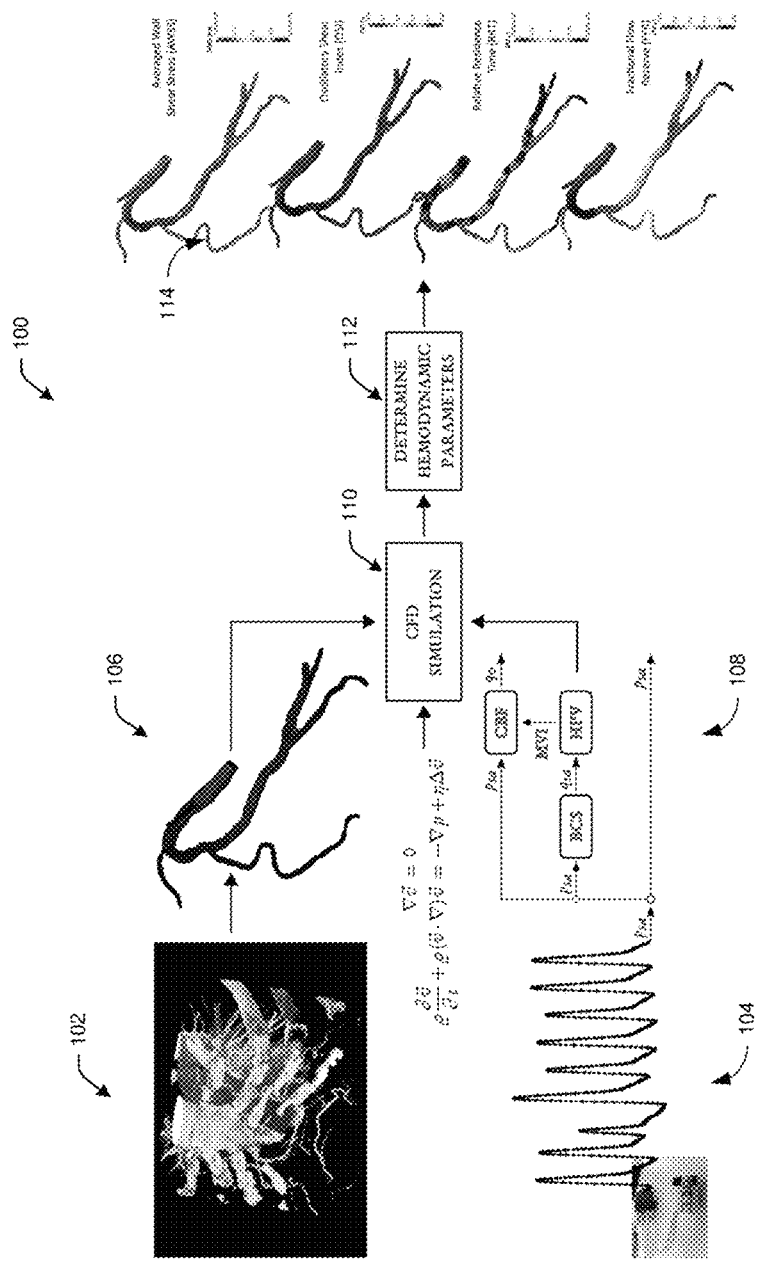
FIG. 1 is a schematic diagram of a method for patient-specific modeling of hemodynamic parameters in coronary arteries in accordance with one or more example embodiments of the disclosure.

This disclosure relates to, among other things, devices, systems, methods, computer-readable media, techniques, and methodologies for non-invasive patient-specific modeling of coronary artery blood flow from volumetric imaging data and continuous arterial pressure data. Volumetric data of a patient's coronary arteries may be captured using non-invasive medical imaging techniques such as computed tomography angiography (CTA) or magnetic resonance angiography (MRA). The volumetric data may be used to create an anatomical model of the patient's coronary arteries suitable for a computational fluid dynamics (CFD) simulation. Continuous arterial pressure data may be derived using non-invasive techniques. The continuous arterial pressure data may be used to determine boundary conditions for the CFD simulation. Patient-specific CFD simulations may be performed using the coronary artery anatomical model, with the inlet and outlet boundary conditions determined from continuous arterial pressure data. Patient-specific hemodynamic parameters in the coronary arteries may be derived from the CFD simulations and may be used to characterize/assess cardiovascular disease, such as the functional assessment of stenosis in the patient.

A CFD simulation may be performed using a patient-specific coronary artery anatomical model derived from medical imaging data and patient-specific boundary conditions derived from continuous arterial pressure data to determine patient-specific hemodynamic parameters in a patient's coronary arteries. In embodiments, a three-component model may be used to determine coronary artery inflow boundary conditions for the CFD simulation. The three-component model may include a blood circulatory system (BCS) component that describes systemic and pulmonary blood circulation, a heart chambers pressure-volume (HPV) component that describes the relationship between ventricular or atrial pressure and volume, and a coronary blood flow (CBF) component that describes coronary tree blood circulation. The three-component model may allow for determining the volumetric flow rate waveform at the inlet of the patient's coronary arteries. The determined volumetric flow rate waveform at the inlet of a patient's coronary arteries may be used to determine coronary artery outflow boundary conditions for the CFD simulation. For example, the volumetric flow rate waveform at the inlet of a patient's coronary arteries may be used to determine the volumetric flow rate waveform at the outlet of the patient's coronary arteries using Murray's law or a similar allometric scaling law (see Sherman T (1981) On connecting large vessels to small—the meaning of murray's law. Journal of General Physiology, 78(4):431-453.).

The patient-specific modeling of coronary artery blood flow in accordance with this disclosure may utilize techniques that provide advantages over existing methods. For example, the constructed patient-specific anatomical model may only model the patient's coronary arteries. That is, the constructed patient-specific anatomical model may not include, for example, reconstruction of the patient's aorta or an estimation of heart chamber volume. This may reduce numerical complexity and simulation time. Additionally, the boundary conditions may be derived from noninvasively measured continuous arterial pressure data. Advantages of using pressure data to derive boundary conditions include the ease with which pressure may be measured relative to other parameters typically used to determined boundary conditions (e.g., velocity, mass flux) and the robustness of pressure measurements, which are not vitiated by excessive error even when measured noninvasively and in a location far from the heart.

Throughout this disclosure, reference is made to modeling coronary arteries and coronary artery blood flow. It is to be understood that coronary arteries may include not only the two main coronary arteries but also arterial branches depending therefrom and any plaques contained therein unless the context clearly dictates otherwise.

Figure 2:
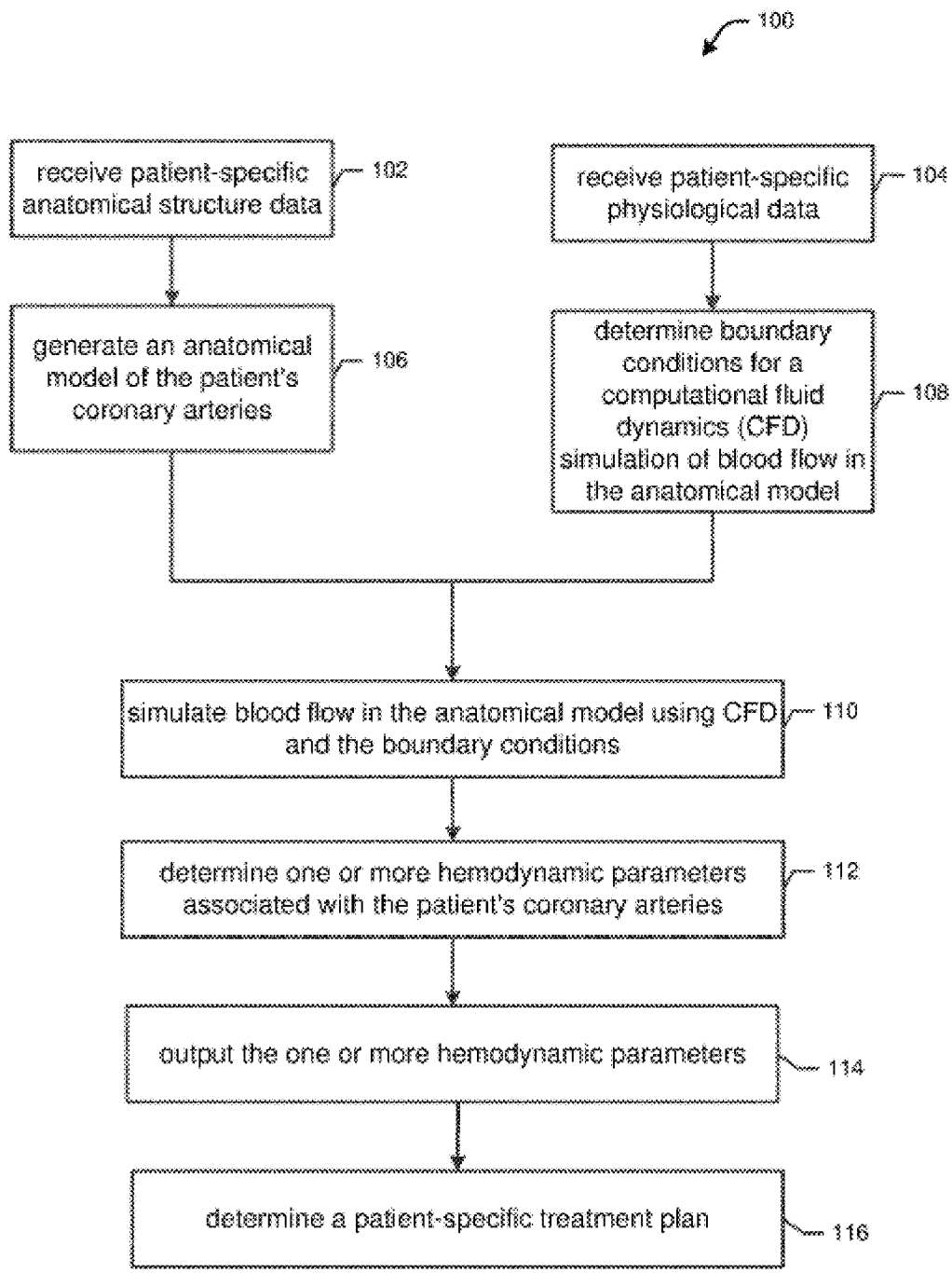
FIG. 2 is a schematic block diagram of a method for patient-specific modeling of hemodynamic parameters in coronary arteries in accordance with one or more example embodiments of the disclosure.

FIGS. 1 and 2 illustrate a method 100 for patient-specific modeling of hemodynamic parameters in coronary arteries in accordance with one or more example embodiments of the disclosure. The method 100 may be performed within a computer or a computer system.

A computer may include one or more non-transitory computer-readable storage medium that store instructions that, when executed by a processor, may perform any of the actions described herein for patient-specific modeling of hemodynamic parameters in coronary arteries. The computer may be, or the computer system may include, a desktop or portable computer, a mobile device (e.g., smartphone), a cloud-based computing system, a server, or any other computer. A computer may include a processor, a read-only memory (ROM), a random access memory (RAM), an input/output (I/O) adapter for connecting peripheral devices (e.g., an input device, output device, storage device, etc.), a user interface adapter for connecting input devices such as a keyboard, a mouse, a touch screen, and/or other devices, a communications adapter for connecting the computer to a network, and a display adapter for connecting the computer to a display. A display may be used to display any calculated hemodynamic parameters to a user (e.g., display images or three-dimensional models of a patient's coronary arteries overlaid with determined hemodynamic parameters).

In step 102, a computer system may receive patient-specific anatomical structure data. A computer system may receive the patient-specific anatomical structure data (e.g., image data acquired by a CT scanner or an X-ray device) over a communication network and/or from a computer readable storage medium.

The patient-specific anatomical structure data may be 2D or 3D images (volumes) of a patient's circulatory system. The images may include at least a portion of, or the entirety of, the patient's coronary arteries. The images may or may not include other anatomical structures such as the patient's heart, aorta, and the like. The patient-specific anatomical structure data may be obtained noninvasively using various noninvasive medical imaging modalities. For example, the data may be obtained using computed tomography (CT), computed tomography angiography (CTA), magnetic resonance imaging (MRI), or magnetic resonance angiography (MRA). Alternatively, the patient-specific anatomical structure data may be obtained using various invasive imaging methods such as rotational angiography, dynamic angiography, or digital subtraction angiography.

The received patient-specific anatomical structure data may be preprocessed by a user and/or by the computer system before further use. Preprocessing may include, for example, checking for misregistration, inconsistencies, or blurring in the captured image data, checking for stents shown in the captured image data, checking for other artifacts that may prevent the visibility of lumens of the coronary arteries, checking for sufficient contrast between anatomical structures (e.g., the aorta, the main coronary arteries, other blood vessels, and other portions of the patient). During the preprocessing, the user and/or computer system may be able to correct certain errors or problems with the data. Preprocessing may also include using image processing techniques on the received patient-specific anatomical structure data to prepare the data for use in generating an anatomical model (e.g., preparing the data for segmentation). The image processing may include, for example, adjusting contrast levels between different anatomical structures (e.g., the heart, the aorta, the coronary arteries, other vasculature, atherosclerotic plaques, etc.) in the images, smoothing of anatomical structures (e.g., applying a smoothing filter), and the like.

In step 104, a computer system may receive patient-specific physiological data. A computer system may receive the patient-specific physiological data over a communication network and/or from a computer readable storage medium.

The patient-specific physiological data may include continuous arterial pressure data (e.g., a continuously recorded blood pressure waveform). Continuous arterial blood pressure is time-varying and measured in real-time without any interruptions (e.g., continuously). In some embodiments, a continuously recorded blood pressure waveform may be obtained for a time period of approximately one (1) minute or a time period within a range of one (1) minute to two (2) minutes, although other continuous time periods may be used. The continuous arterial pressure data may be obtained without a percutaneous procedure (e.g., noninvasively). For example, the data may be obtained using a Nexfin™ monitor, a ClearSight™ monitor, a CNAP™ monitor, a Finapres® NOVA monitor or successor systems (e.g., Finometer® and Portapres® monitors), or other similar noninvasive continuous arterial pressure measuring devices. Alternatively, the continuous arterial pressure data may be obtained using various invasive methods such as arterial catheterization. The continuous arterial pressure data may undergo data processing (e.g., signal processing) to prepare the data for use in determining boundary conditions for a CFD simulation and/or simulating blood flood in an anatomical model using CFD. For example, pressure signals may be extracted from the continuous arterial pressure data.

The patient-specific physiological data may include physiological data other than continuous arterial pressure data, such as the patient's heart electrical activity, baseline heart rate, height, weight, hematocrit, stroke volume, and the like. Generally, any physiological data may undergo data processing (e.g., signal processing) to prepare the data for use in determining boundary conditions for a CFD simulation and/or simulating blood flood in an anatomical model using CFD.

Figure 3:
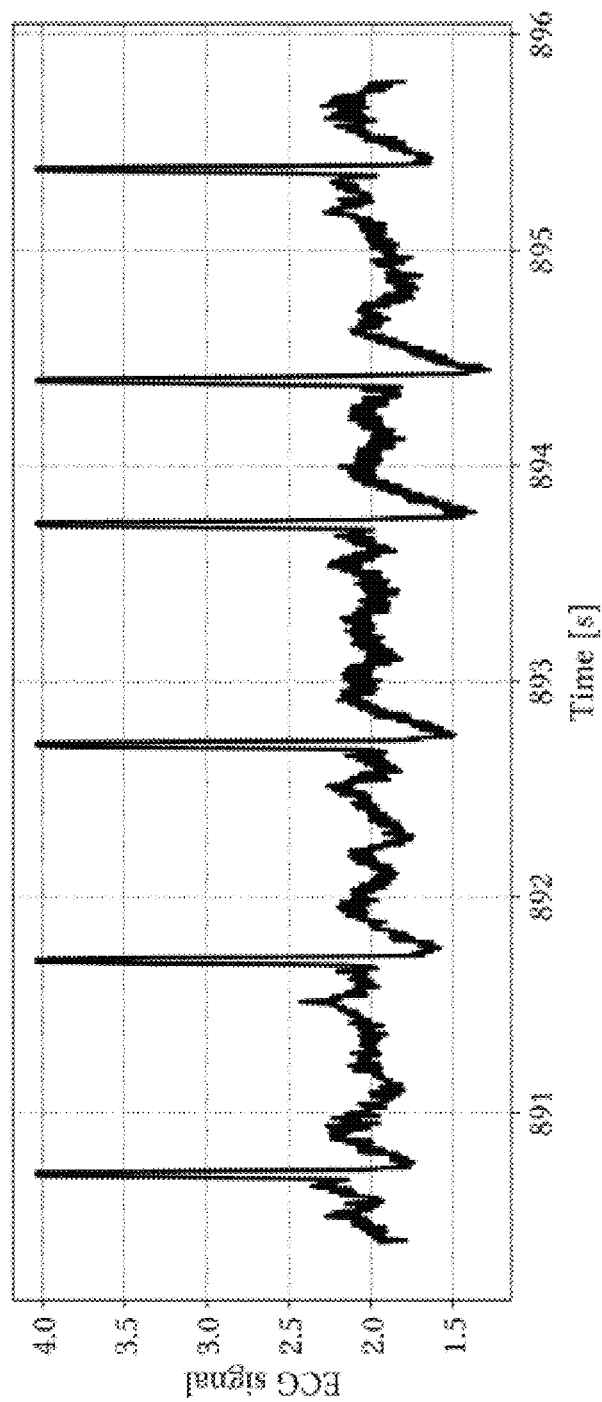
FIG. 3 is an exemplary electrocardiogram recording of a patient.

The physiological data may include, for example, a continuous recording of an electrocardiography (ECG) signal from the patient, an example of which is shown in FIG. 3. The ECG signal may be used to directly reconstruct temporal heart cycle parameters such as a heart rate variability (e.g., an RR-interval). In the example of FIG. 3, the calculated average RR-interval for the patient's recording is 0.897 s. The RR-interval may be used, for example, in determining boundary conditions for a CFD simulation.

Figure 4:
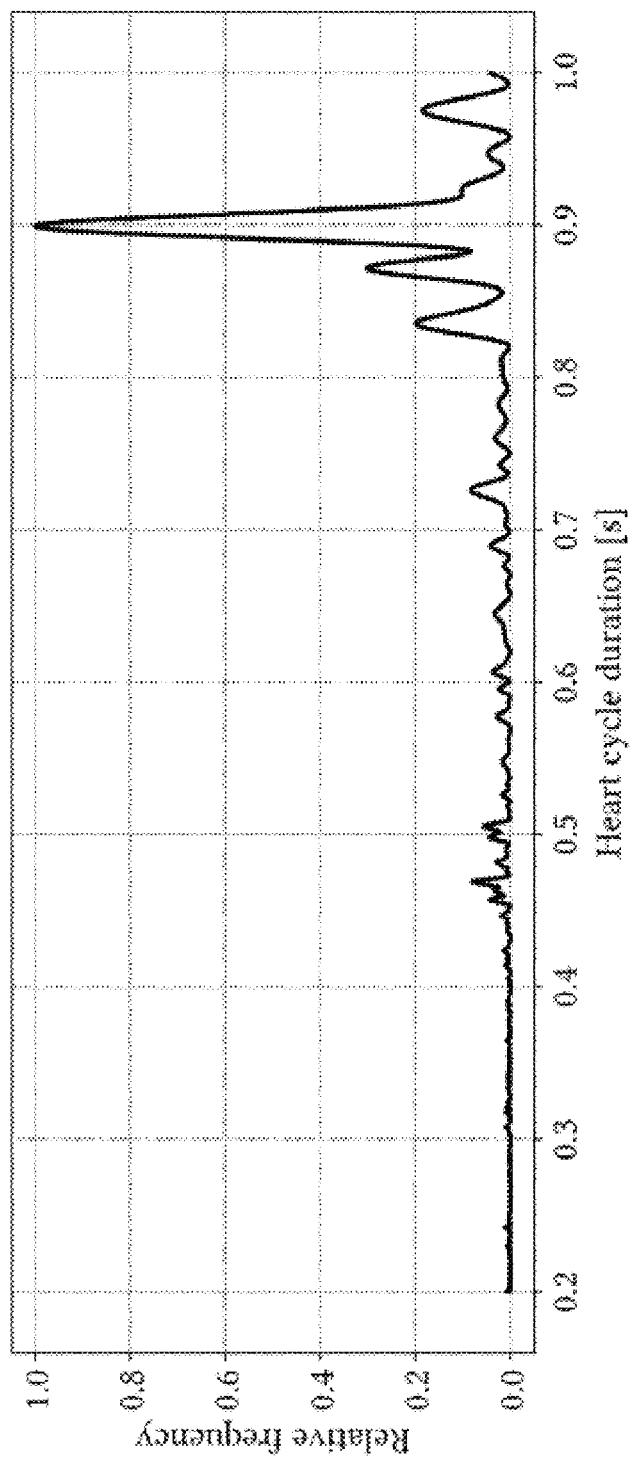
FIG. 4 is an exemplary Lomb-Scargle periodogram of a patient's heart cycle.

The physiological data may include, for example, aortic pressure course. Aortic pressure course may be used to indirectly determine temporal heart cycle parameters when a patient's ECG signal is unavailable, although this is slightly less accurate when compared to ECG. A Lomb-Scargle algorithm may be used to construct a Lomb-Scargle periodogram of a patient's heart cycle from aortic pressure course, an example of which is shown in FIG. 4. The Lomb-Scargle algorithm may be used to find and test the significance of weak periodic signals with uneven temporal sampling (see Townsend R H D (2010) Fast calculation of the Lomb-Scargle periodogram using graphics processing units. The Astrophysical Journal, Supplement Series, Vol. 191, 247-253.). In the example of FIG. 4, the calculated RR-interval for the patient's pressure recording using the Lomb-Scargle algorithm is 0.901 s. The RR-interval calculated using the Lomb-Scargle algorithm is slightly different than the RR-interval determined from ECG data, but the difference is less than 0.5%.

In step 106, a computer system may generate a patient-specific anatomical model of the patient's coronary arteries from the received patient-specific anatomical structure data. The patient-specific anatomical model may be a 3D geometric model of the patient's coronary arteries. The constructed patient-specific anatomical model may only model the patient's coronary arteries. That is, the constructed patient-specific anatomical model may not include, for example, reconstruction of the patient's heart, aorta, non-coronary artery related vasculature, or other tissues.

Received patient-specific anatomical structure data (e.g., anatomical images) may include regions of varying optical density that correspond to different anatomical structures such as the aorta, the main coronary arteries, coronary artery branches, myocardium, and the like. The locations of anatomical structure surfaces may be determined based on the contrast (e.g., relative darkness and lightness) between different anatomical structures. The contrast between anatomical structures may also enable the selective modeling of certain anatomical features (e.g., coronary arteries) while excluding other anatomical features from the generated model (e.g., the heart).

The process of forming the patient-specific anatomical model is generally referred to as segmentation. Segmentation may be performed automatically by the computer system with or without user input. In order to generate the patient-specific anatomical model, the coronary arteries may be segmented in the patient-specific anatomical structure data using any suitable coronary artery segmentation method. Methods for generating an anatomical model of a patient's coronary arteries (e.g., coronary artery segmentation methods) are described, for example, in U.S. Patent Application Nos. 2010/006776 and 2012/0072190 and U.S. Pat. Nos. 7,860,290, 7,953,266, and 8,315,812, each of which are incorporated herein by reference in their entirety for all purposes. The segmented coronary arteries may be reviewed and/or corrected by the computer system and/or a user, if necessary (e.g., to correct the segmentation if there are any errors such as missing or inaccurate coronary arteries or branches extending therefrom).

The patient-specific anatomical model (e.g., 3D geometric model) may be represented as a surface mesh. The surface mesh may represent the external boundary of segmented structures such that their shape is represented as a set of connected vertices (e.g., a mesh). By using such a representation, shape constraints may be imposed using mesh-based shape metrics or statistics. A deformable model, such as an Active Mesh Model (AMM) (see Dufour, A. et al., Segmenting and tracking fluorescent cells in dynamic 3-D microscopy with coupled active surfaces. IEEE Transactions on Image Processing, 14(9), 1396-1410, 2005; Dufour, A. et al., J.-C. 3-D active meshes: fast discrete deformable models for cell tracking in 3-D time-lapse microscopy. IEEE Transactions on Image Processing, 20(7), 1925-1937, 2011.), may be a starting point for creating the patient-specific anatomical model. AMM is 3D extension of the active contour model (ACM) used in image analysis techniques (see Kass, M. et al., Active contour models. Int. J. of Computer Vision 1(4), 321-331, 1988.). In AMM-based methods, segmented structures may be represented as closed surfaces (fronts, meshes) that evolve with a speed computed from both image-dependent data and image-independent geometric properties.

In embodiments, the process for forming the patient-specific anatomical model may include, for example, segmenting visible plaques in coronary arteries using an AMM-based method, selecting by a computer and/or user root points (e.g., starting points) for the left and right coronary arteries, segmenting the coronary arteries using the AMM-based method and selected root points, and verifying and/or correcting the geometry of the segmented plaques and arteries.

After segmentation, a user and/or computer system may post-process the patient-specific anatomical model to prepare the model for CFD simulations. This may include, for example, determining centerlines for the coronary arteries and their branches, determining cross-sectional areas of the coronary arteries and their branches, creating models of inflow boundaries (e.g., the boundaries through which flow is directed into the coronary arteries) and outflow boundaries (e.g., the boundaries through which flow is directed out of the coronary arteries and/or coronary artery branches) such that the inflow boundaries and the outflow boundaries are perpendicular to the determined centerlines, thereby permitting boundary condition application, and smoothing the model (e.g. smoothing any ridges, points, etc). The post-processing of the patient-specific anatomical model may be reviewed and/or corrected by the computer system and/or the user, if necessary.

In step 108, a computer system may determine boundary conditions for a computational fluid dynamics (CFD) simulation of blood flow in the anatomical model. At least some of the boundary conditions may be determined using received patient-specific physiological data, such as received continuous arterial pressure data. The boundary conditions may include coronary circulation inflow and outflow boundary conditions.

Figure 5:
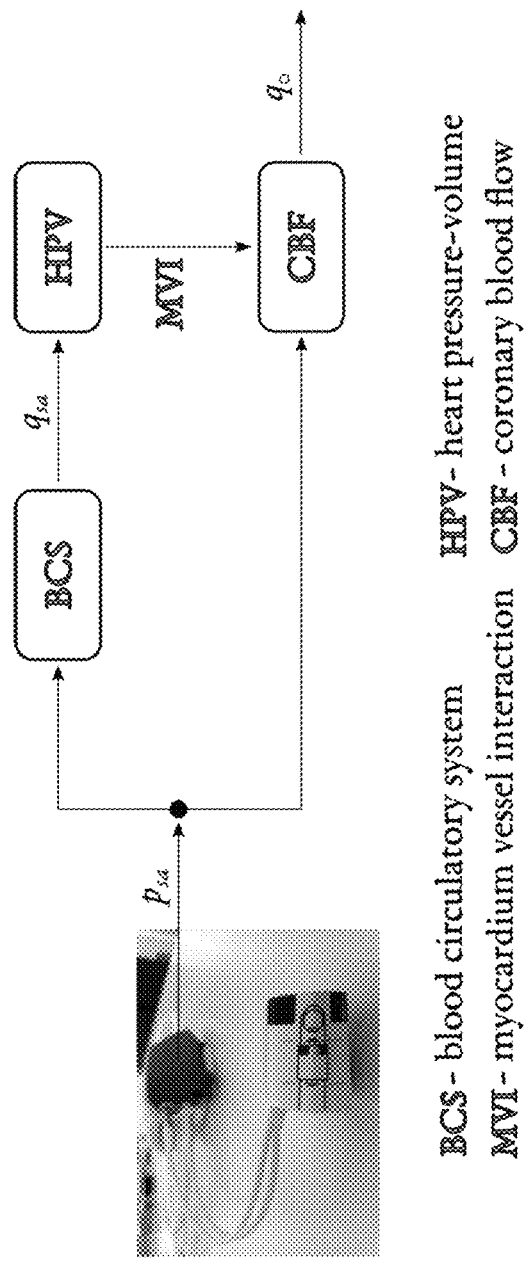
FIG. 5 is a schematic of a three-component model for use in determining coronary circulation boundary conditions.
Figure 18:
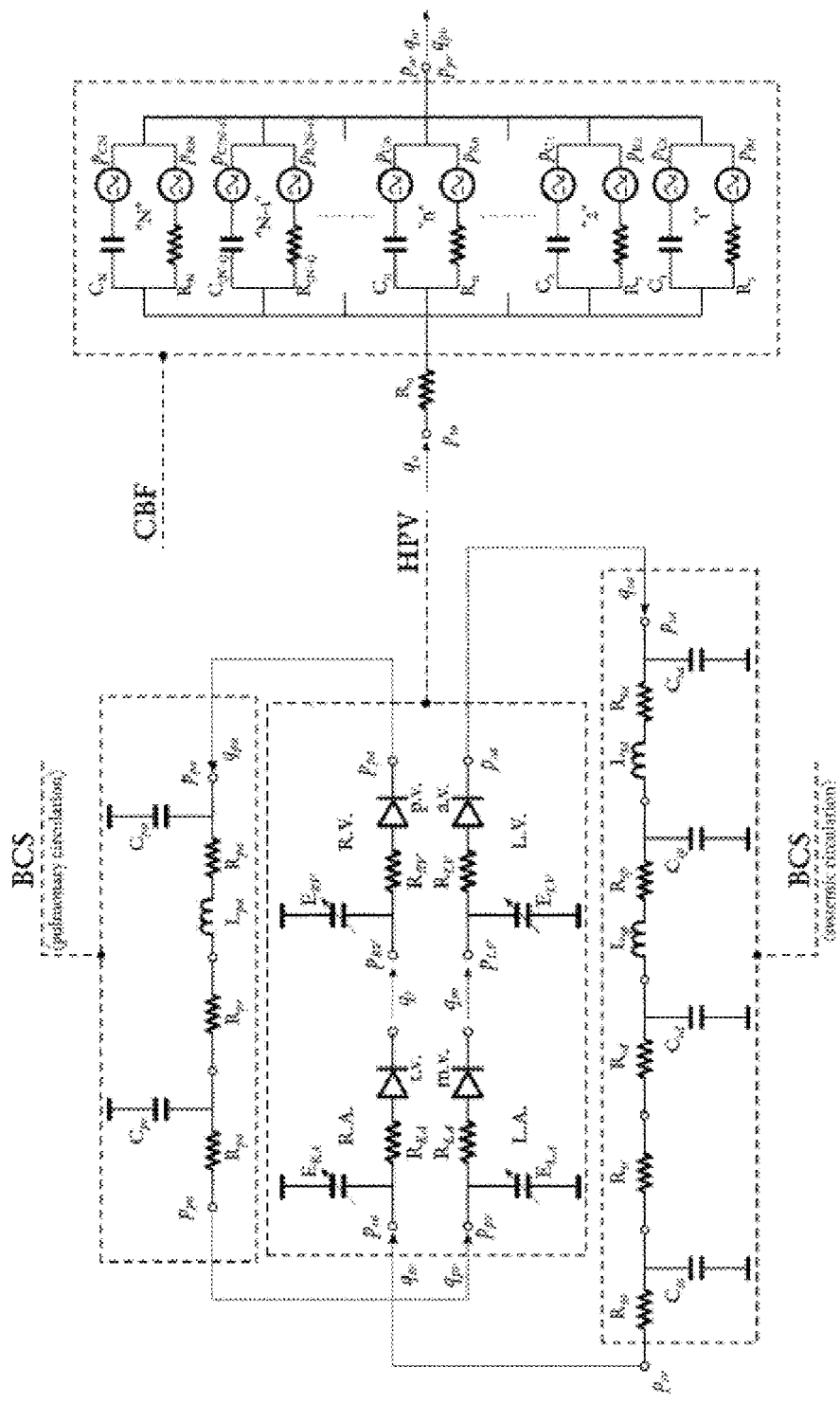
FIG. 18 illustrates in detail a three-component model for use in determining coronary circulation boundary conditions including: a blood circulatory system (BCS) (pulmonary and systemic circulation) model component, a heart pressure-volume (HPV) model component, and a coronary blood flow (CBF) model component.

A three-component model, illustrated in FIG. 5, may be used in determining coronary circulation boundary conditions. The three-component model may include a blood circulatory system (BCS) component that describes systemic and pulmonary blood circulation, a heart pressure-volume (HPV) component that describes a cardiac pressure-volume loop, and a coronary blood flow (CBF) component that describes coronary artery blood circulation (see FIG. 5). Each of the BCS, HPV, and CBF components may be selected from various models of each component, which are discussed in more detail below. The three-component model may take as an input the pressure waveform $p_{sa}(t)$, which may be derived from the patient-specific continuous recording of arterial pressure (e.g., patient-specific continuous arterial pressure data). An exemplary embodiment of a three-component model is shown in FIG. 18.

Figure 20:
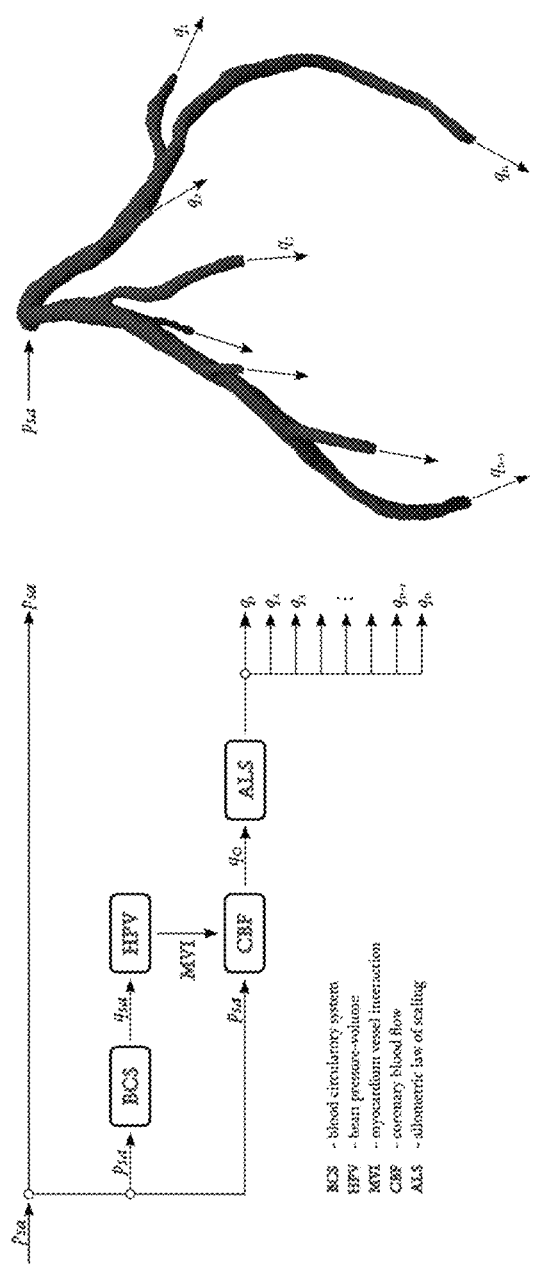
FIG. 20 illustrates a schematic for determining coronary circulation inflow and outflow boundary conditions.

The three-component model may be used to directly determine inflow boundary conditions, such as the volumetric flow rate waveform at the inlet of the patient's coronary arteries (see FIG. 20). The three-component model may be used to indirectly determine outflow boundary conditions, such as the volumetric flow rate waveform at the outlet of the patient's coronary arteries (see FIG. 20). For example, the volumetric flow rate waveform at the inlet of the patient's coronary arteries may be used to determine the volumetric flow rate waveform at the outlet of the patient's coronary arteries using an allometric law of scaling (ALS) such as Murray's law, which describes a relationship between blood flow and vessel radius (see FIG. 20) (see Freund J et al., (2012) Fluid flows and forces in development: functions, features and biophysical principles. Development, 139(7):1229-1245; Newberry M et al., V M (2015) Testing foundations of biological scaling theory using automated measurements of vascular networks. Public Library of Science Computational Biology, 11(8):e1004455; Sherman T (1981) On connecting large vessels to small—the meaning of murray's law. Journal of General Physiology, 78(4):431-453; Algranati D et al. (2010) Mechanisms of myocardium-coronary vessel interaction. American Journal of Physiology. Heart and Circulatory Physiology, Vol. 298, No. 3, H861-H873.). According to Murray's law, blood flow is proportional to $r^3$ in every vessel of a Murray system.

Figure 6:
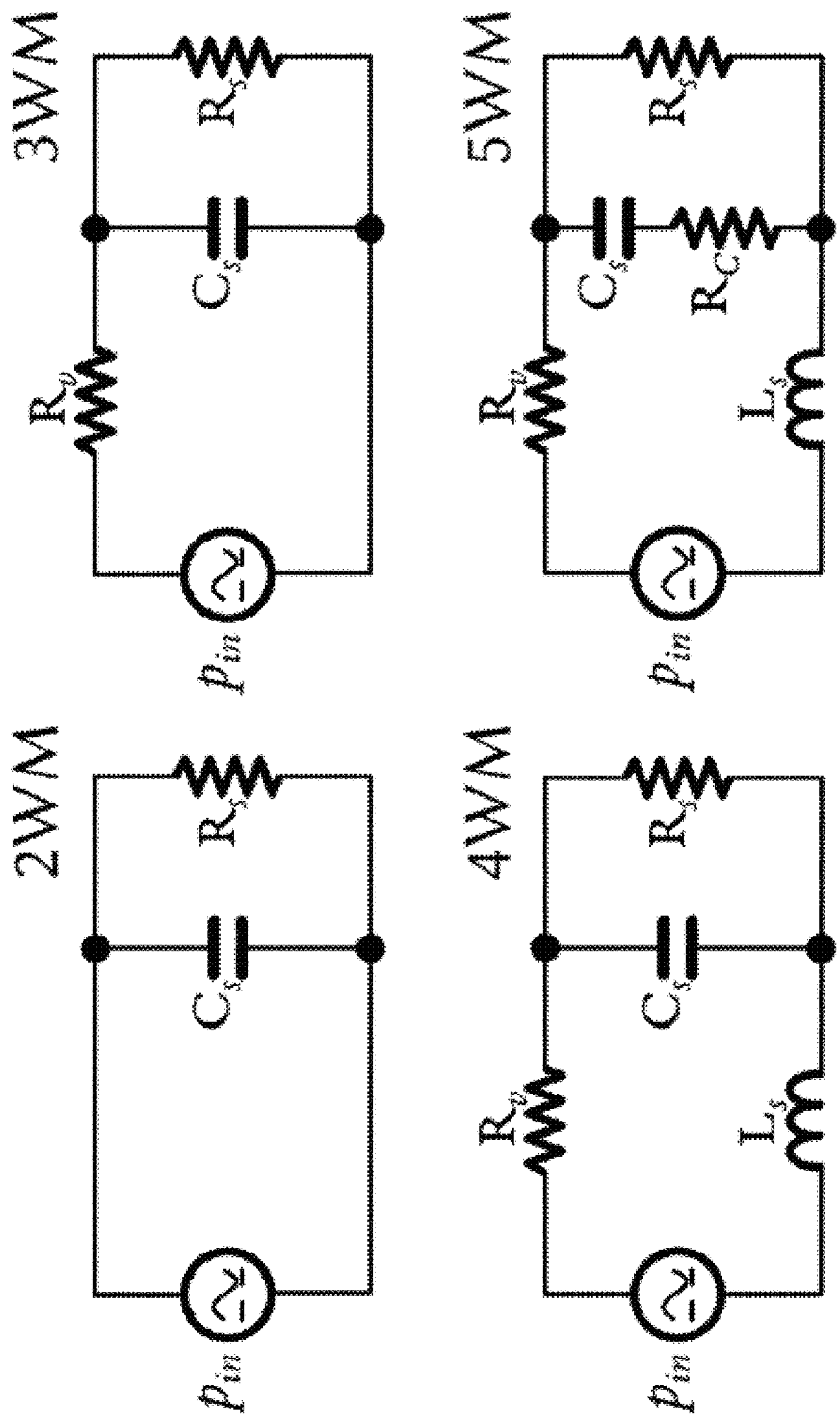
FIG. 6 illustrates four different Windkessel models, specifically two-, three-, four- and five-element Windkessel models (2WM, 3WM, 4WM, 5WM), suitable for use in a blood circulatory system (BCS) component model.
Figure 7:
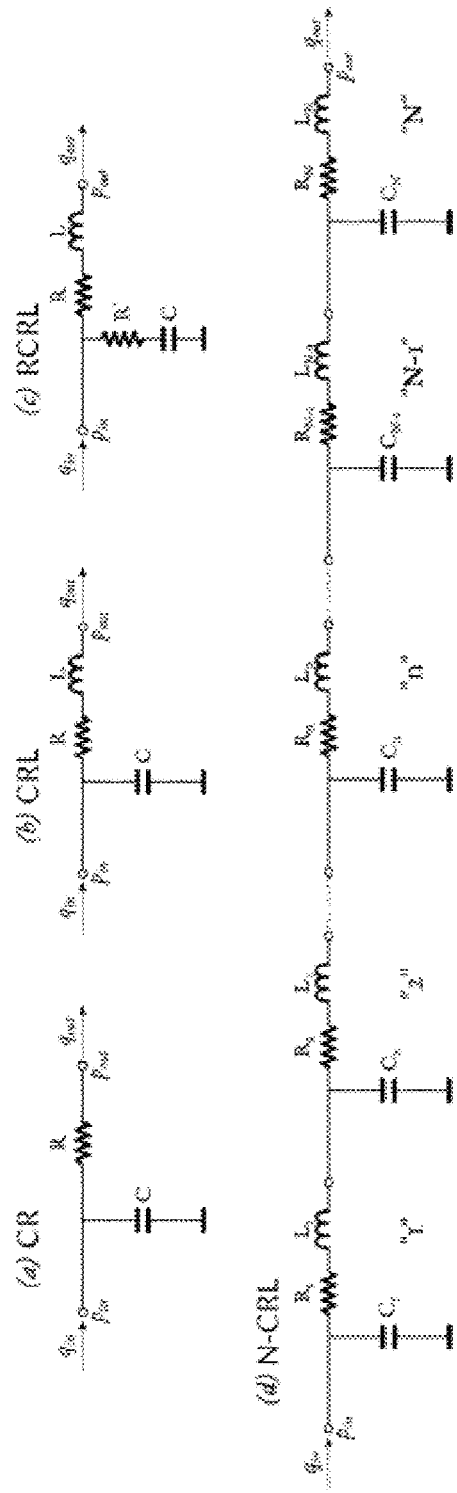
FIG. 7 illustrates several functional blocks (a-c) and an exemplary multi-block system (d) composed of functional block (b) for use in a blood circulatory system (BCS) component model.

The blood circulatory system (BCS) component describes systemic and pulmonary blood circulation. Blood circulation may be modeled, for example, using a two-, three-, four-, or five-element Windkessel (2WM, 3WM, 4WM, 5WM) lumped functional block, which are shown in FIG. 6 (see Garcia D et al. (2009) Impairment of coronary flow reserve in aortic stenosis. Journal of Applied Physiology, Vol. 106, No. 1, 113-121; Li J K-J (2000) The Arterial Circulation. Physical Principles and Clinical Applications, Springer, New York; Ostadfar A (2016) Biofluid mechanics. Principles and applications. Elsevier; Pappano A et al. (2013) Cardiovascular physiology. Elsevier; Stergiopulos N et al. (1996) Determinants of stroke volume and systolic and diastolic aortic pressure. American Journal of Physiology, Vol. 270, No. 6, Pt. 2, H2050-H2059; Westerhof N et al. (2009) The arterial windkessel. Medical & Biological Engineering & Computing, Vol. 47, No. 2, 131-141; Zamir M (2005) The physics of coronary blood flow. Springer-Verlag.). Pulmonary and systemic circulation may be modeled, in a preferred embodiment, using one of the lumped parameter models shown in FIG. 7, while overall blood circulation may be modeled using a multi-compartment model shown in FIG. 8.

Figure 8:
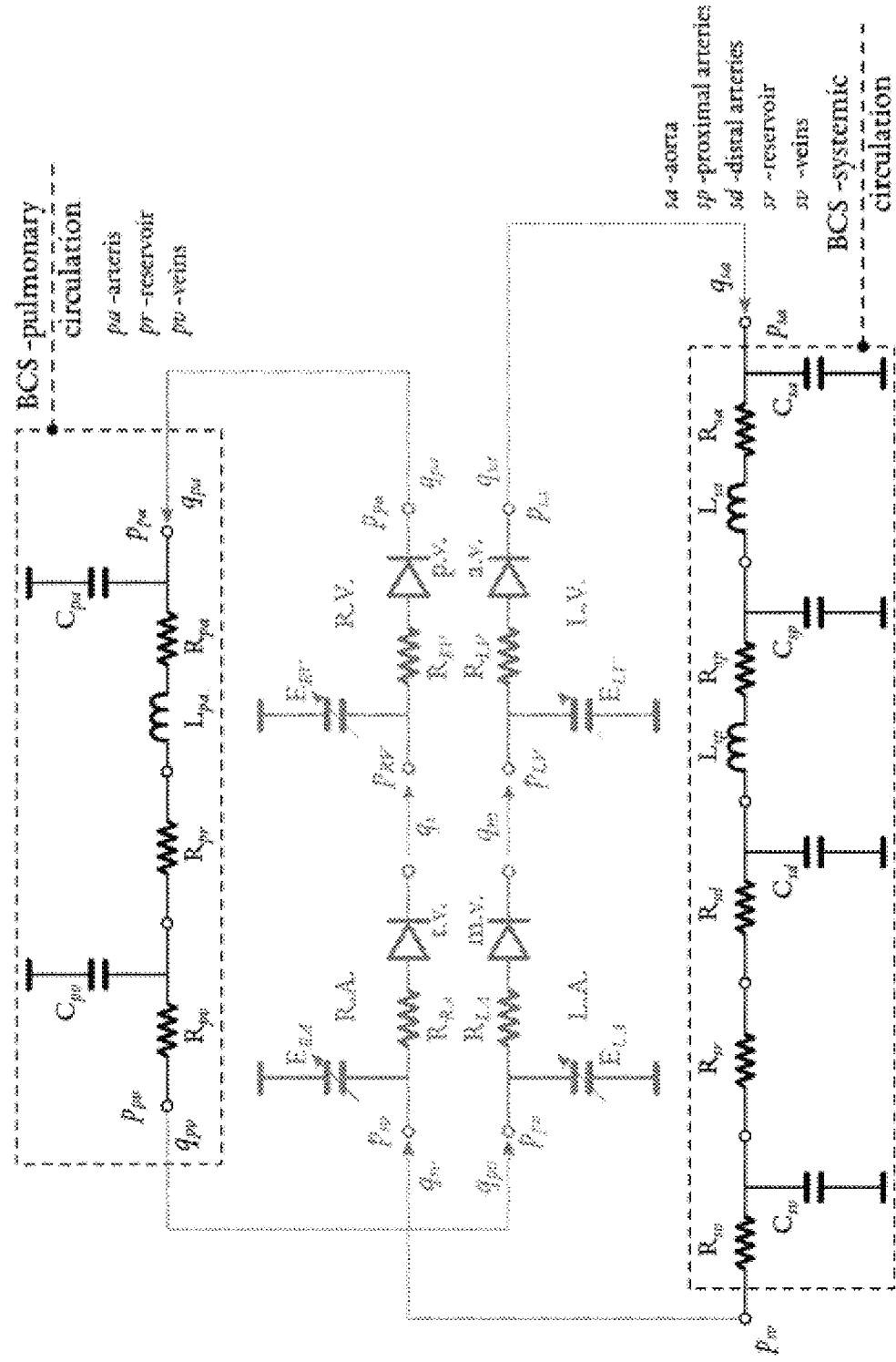
FIG. 8 illustrates a blood circulatory system (BCS) model comprising systemic and pulmonary circulation elements, and its relation to an HPV component.
Figure 9:
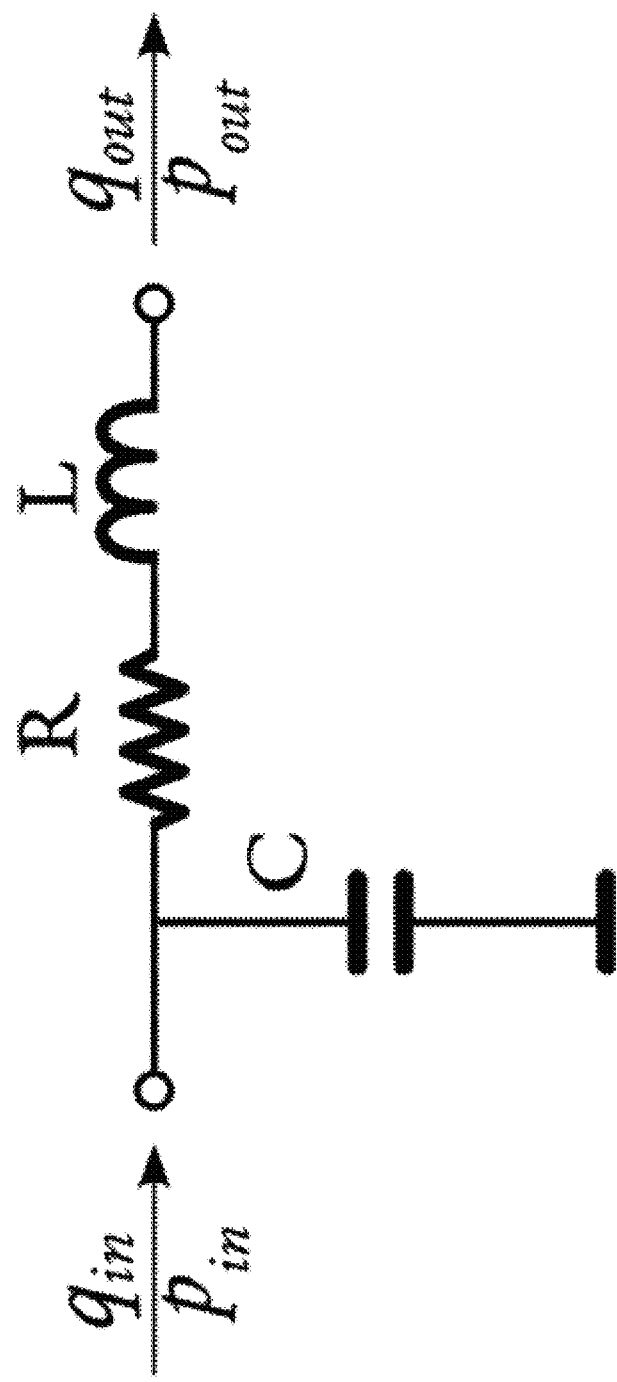
FIG. 9 illustrates a lumped parameter functional block comprising resistance, inertance, and capacitance (RLC) parameters that is suitable for use in a blood circulatory system (BCS) component model.

In an embodiment, the blood circulatory system model component (e.g. the systemic and pulmonary circulation model) is built upon a resistance (R)—inertance (L)—capacitance (C) lumped parameter functional block RLC shown in FIG. 9. In the lumped parameter functional block of FIG. 9, the block inputs (in) and output (out) are related in time (t):

$$q_{in} = C\frac{dp_{in}}{dt} + q_{out},$$

$$p_{in} = R \cdot q_{out} + L\frac{dq_{out}}{dt} + p_{out},$$

where: q is flow rate and p is the pressure of flowing blood in a selected compartment. As shown in FIG. 8, a pulmonary circulation model contains three compartments in the form of arteries (C=$C_{pa}$, R=$R_{pa}$, L=$L_{pa}$), pulmonary reservoir (C=0, R=$R_{pr}$, L=0), and veins (C=$C_{pv}$, R=$R_{pv}$, L=0), which leads to six equations (3×2=6). The systemic circulation model contains five compartments, namely aorta (C=$C_{sa}$, R=$R_{sa}$, L=$L_{sa}$), proximal conducting arteries (C=$C_{sp}$, R=$R_{sp}$, L=$L_{sp}$), distal muscular arteries (C=$C_{sd}$, R=$R_{sd}$, L=0), systemic reservoir (C=0, R=$R_{sr}$, L=0), and veins (C=$C_{sv}$, R=$R_{sv}$, L=0), which leads to ten equations (5×2=10). The resulting system of sixteen equations may be solved numerically.

Figure 10:
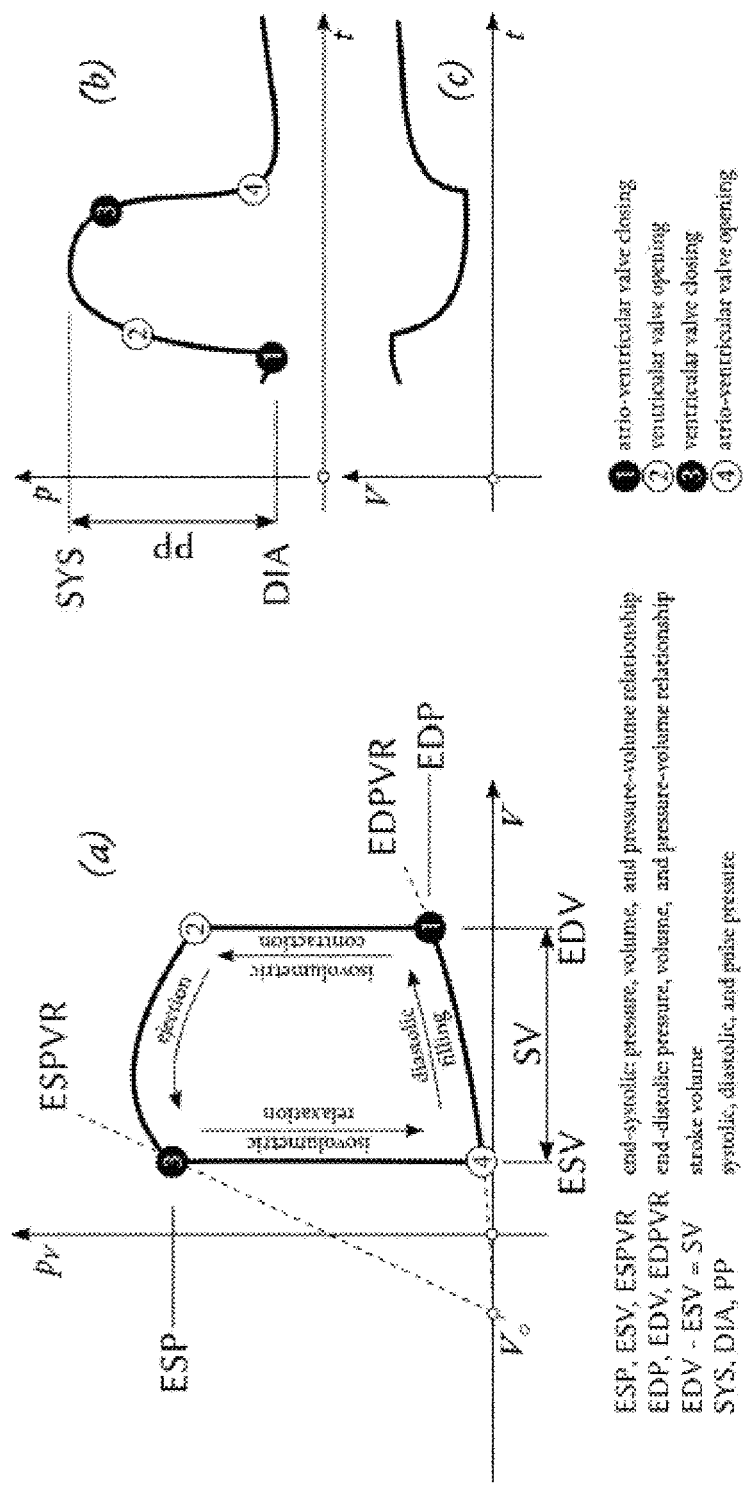
FIG. 10 illustrates schematic diagrams of (a) a heart-ventricle pressure-volume loop, (b) aortic pressure plotted as a function of time, and (c) ventricular volume plotted as a function of time.
Figure 11:
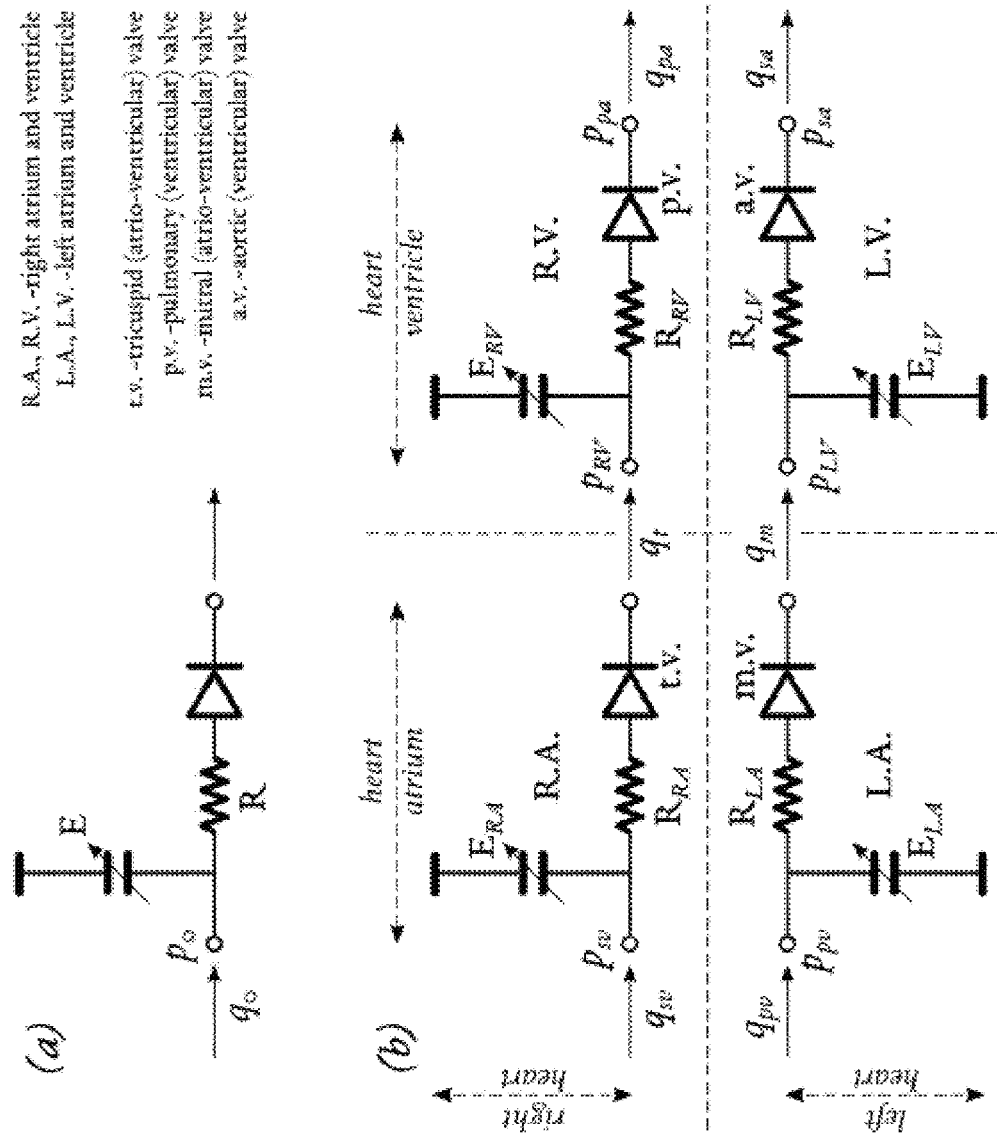
FIG. 11 illustrates a functional block (a) and a whole heart pressure-volume (HPV) component model (b).

The heart ventricle or atrium pressure-volume (HPV) component describes a cardiac pressure-volume loop. The heart cycle consists of four phases, as shown in FIG. 10 (see Barrett K E et al. (2016) Ganong's review of medical physiology, McGraw-Hill; Mohrman D et al. (2013) Cardiovascular physiology. McGraw-Hill, Lange, New York; Pappano A et al. (2013) Cardiovascular physiology. Elsevier.). Many different models may be used for the isovolumetric systolic and diastolic phases such as, for example, a time varying-elastance model (TVE), a time-varying compliance (TVC) model, or other models (see Garcia D et al. (2009) Impairment of coronary flow reserve in aortic stenosis. Journal of Applied Physiology, Vol. 106, No. 1, 113-121; Lankhaar J W et al. (2009) Modeling the instantaneous pressure-volume relation of the left ventricle: a comparison of six models. Annals of biomedical engineering, Vol. 37, No. 9, 1710-1726; Stergiopulos N et al. (1996) Determinants of stroke volume and systolic and diastolic aortic pressure. American Journal of Physiology, Vol. 270, No. 6, Pt. 2, H2050-H2059.). FIG. 11 illustrates a functional block for building a heart chambers pressure-volume (HPV) component model (a); and a whole, multi-compartment heart chambers pressure-volume (HPV) component model (b). In a preferred embodiment, the pressure-volume (HPV) component uses a model based on the idea of varying elastance E(t) as a reciprocal of compliance, which may be written in the form:

$$E(t) = \frac{1}{C(t)} = \frac{dp}{dV}$$

Pressure in a heart chamber, during the isovolumetric phase, may be described by the equation:

$$p(t) = E(t) \cdot (V(t) - V_0).$$

where V(t) is the heart chamber volume, and $V_o$ is a volume intercept.

Elastance may be calculated based on convolution of a Archibald Hill function $f_i(t_n) = t_n^{n_i}/(a_i^{n_i} t_n^{n_i})$, which may be written in the form:

$$E_n(t_n) = \frac{E(t_n) - E_{min}}{E_{max} - E_{min}} = A \cdot (f_1(t_n) \cdot (1 - f_2(t_n)))$$

where:

$$t_n = \frac{t \% T}{t_{max}}, \quad t_{max} = t @ E(t) = E_{max},$$

and T is the heart cycle duration according to an RR-interval, which may be determined by ECG or estimated from aortic pressure course. Typical values of time-varying elastance model empirical parameters are provided in the table below (see Stergiopulos N et al. (1996) Determinants of stroke volume and systolic and diastolic aortic pressure. American Journal of Physiology, Vol. 270, No. 6, Pt. 2, H2050-H2059; Faragallah G et al. (2012) A new control system for left ventricular assist devices based on patient-specific physiological demand. Inverse Problems in Science and Engineering, Vol. 20, No. 5, 721-734.).

| $E_{min}$ | $E_{max}$ | $a_1$ | $a_2$ | $n_1$ | $n_2$ |
|---|---|---|---|---|---|
| 0.06 | 2.31 | 0.303 | 0.508 | 1.32 | 21.9 |
| 0.06 | 2.00 | 0.700 | 1.170 | 1.90 | 21.9 |

A time-varying elastance model may only be used during a heart cycle's isovolumetric phases. For the other two heart cycle phases (FIG. 10), blood volume is partially accumulated in the atrium while the rest—followed by the transvalvular pressure gradient—flows out. Therefore, the atrial flow rate balance can be described as:

$$q_{sv} = C_{RA}\frac{dp_{sv}}{dt} + q_t, \quad q_{pv} = C_{LA}\frac{dp_{pv}}{dt} + q_m,$$

and similarly the ventricular flow rate can be described as:

$$-\frac{dV_{RV}}{dt} = q_{pa} - q_t, \quad -\frac{dV_{LV}}{dt} = q_{sa} - q_m.$$

Simultaneously, transvalvular flow can be described as:

$$q_m = \frac{(p_{pv} - p_{LV})}{R_{LA}} H(p_{pv} - p_{LV}), \quad q_{sa} = \frac{(p_{LV} - p_{sa})}{R_{LV}} H(p_{LV} - p_{sa}),$$

$$q_t = \frac{(p_{sv} - p_{RV})}{R_{RA}} H(p_{sv} - p_{RV}), \quad q_{pa} = \frac{(p_{RV} - p_{pa})}{R_{RV}} H(p_{RV} - p_{pa}).,$$

where H is Heaviside step function.

Figure 12:
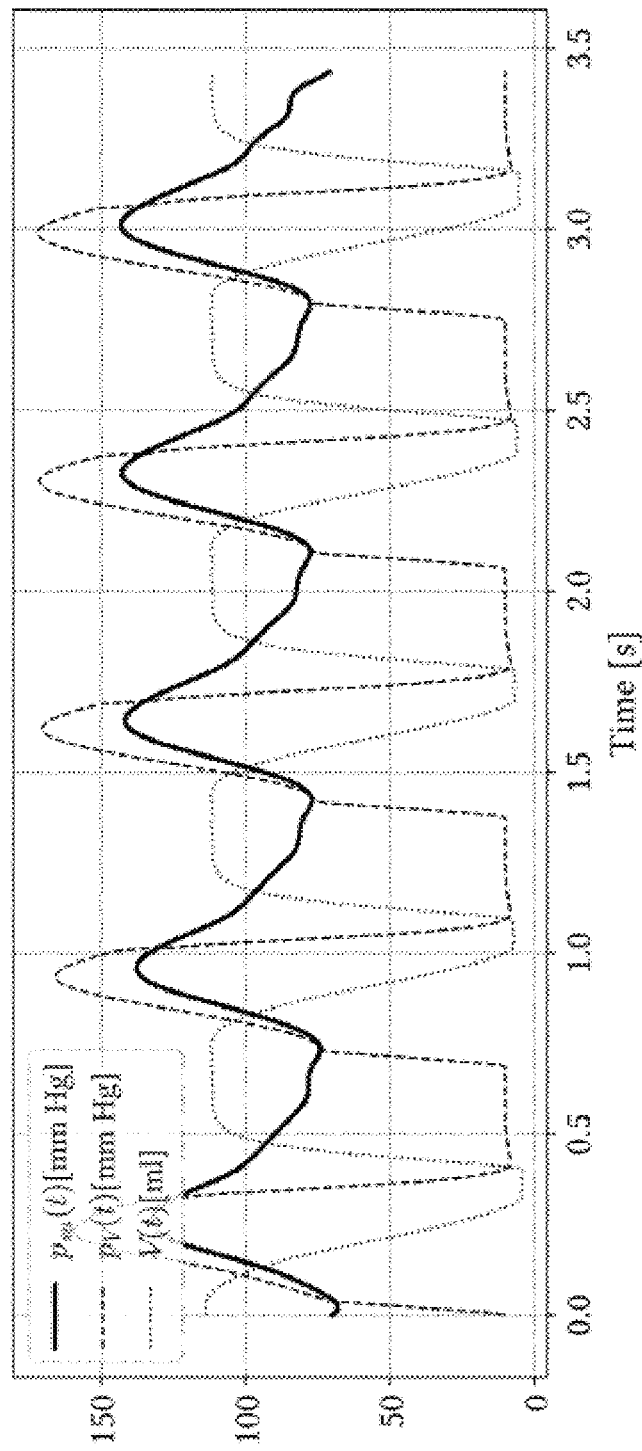
FIG. 12 is a graph showing reconstructed patient-specific heart ventricle volume and pressure during five heart cycles.

In embodiments, a patient-specific calibration (PSC) procedure may be used for the optimal parameter estimation of the HPV and BCS models. The procedure may include: (i) determining initial approximations of model parameters from patient systolic and diastolic pressure levels, gender, age, and heart rate (HR) (see Barrett K E et al. (2016) Ganong's review of medical physiology, McGraw-Hill; Li J K-J (2000) The Arterial Circulation. Physical Principles and Clinical Applications, Springer, New York; Pappano A et al. (2013) Cardiovascular physiology. Elsevier; Zamir M (2005) The physics of coronary blood flow. Springer-Verlag; Maceira A M et al. (2006) Reference right ventricular systolic and diastolic function normalized to age, gender and body surface area from steady-state free precession cardiovascular magnetic resonance. European Heart Journal, Vol. 27, Issue 23, Pages 2879-2888; Maceira A M et al. (2006) Normalized left ventricular systolic and diastolic function by steady state free precession cardiovascular magnetic resonance. Journal of Cardiovascular Magnetic Resonance, Vol. 8, Issue 3, 417-426.), (ii) making corrections based on additional information including smoking habits, fitness habits, and drug use (see Tsanas A et al. (2009) The Windkessel model revisited: a qualitative analysis of the circulatory system. Medical Engineering & Physics, Vol. 31, Issue 5, 581-588.), (iii) solving the models (HPV+BCS), and (iv) and calibrating the parameters by fitting them to the calculated pressure and patient pressure instantaneous recording. In this way, a time-varying elastance model (e.g., applied in the HPV model) in conjunction with a circulation model (BCS) may be used to reconstruct left and right heart instantaneous ventricle volumes (V) and internal pressures ($p_V$) course using a patient's recorded aortic pressure ($p_{sa}$), as shown in FIG. 12.

Figure 13:
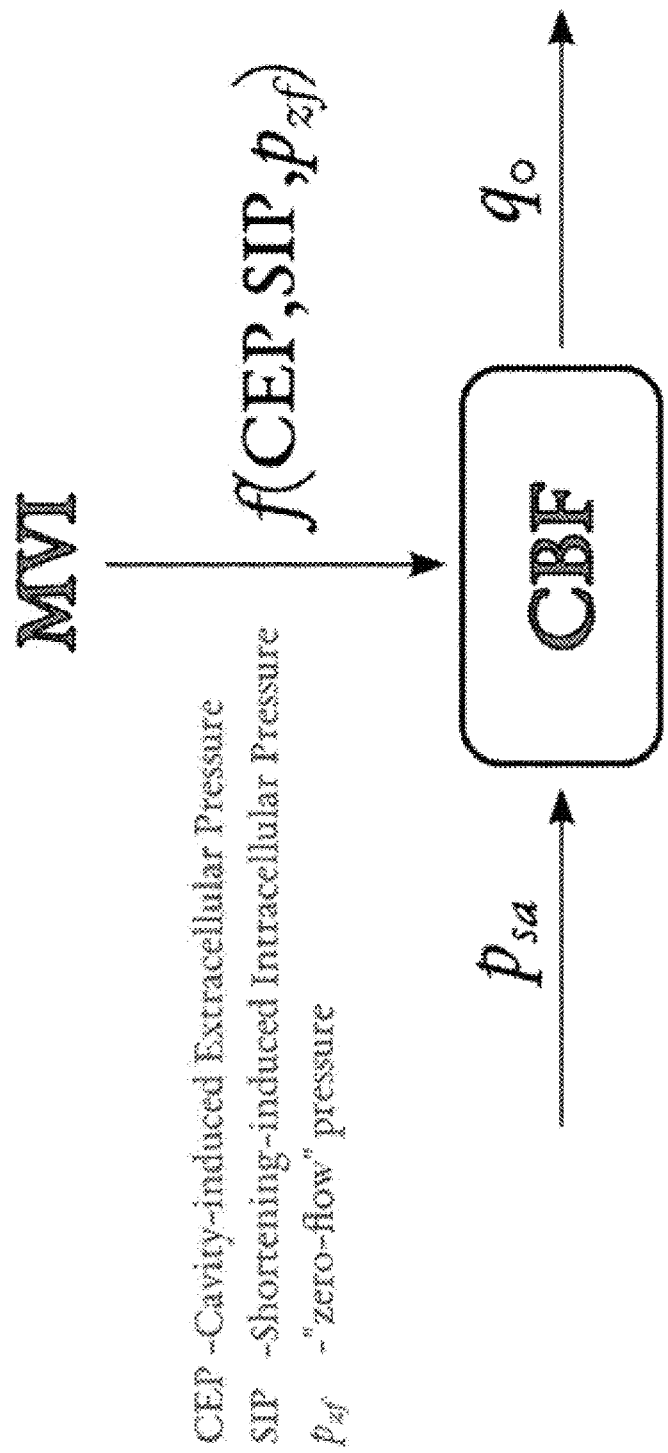
FIG. 13 illustrates a general coronary blood flow (CBF) model concept.

The coronary blood flow (CBF) component describes coronary artery blood circulation, and is shown generally in FIG. 13. The CBF component derives from several conclusions drawn from physiology findings (see Epstein S et al. (2015) Reducing the number of parameters in 1D arterial blood flow modeling: less is more for patient-specific simulations. American Journal of Physiology, Heart and Circulatory Physiology, Vol. 309, No. 1, H222-H234; Kheyfets V O et al. (2016) A zero-dimensional model and protocol for simulating patient-specific pulmonary hemodynamics from limited clinical data. Journal of Biomechanical Engineering, Vol. 138, Issue 12, 1-8; Maruyama Y et al. (1994) Recent advances in coronary circulation. Springer-Verlag, Berlin and Heidelberg; Mohrman D et al. (2013) Cardiovascular physiology. McGraw-Hill, Lange, New York; Ostadfar A (2016) Biofluid mechanics. Principles and applications. Elsevier; Pappano A et al. (2013) Cardiovascular physiology. Elsevier; Zamir M (2005) The physics of coronary blood flow. Springer-Verlag; Algranati D et al. (2010) Mechanisms of myocardium-coronary vessel interaction. American Journal of Physiology. Heart and Circulatory Physiology, Vol. 298, No. 3, H861-H873; Mynard J P et al. (2014) Scalability and in vivo validation of a multiscale numerical model of the left coronary circulation. American Journal of Physiology. Heart and Circulatory Physiology, Vol. 306, No. 4, H517-H528; Westerhof N et al. (2006) Cross-talk between cardiac muscle and coronary vasculature. Physiological Reviews, Vol. 86, No. 4, 1263-1308.), which include: (i) the main factor forcing flow in the coronary arteries is the instantaneous pressure in the aorta $p_{sa}(t)$; (ii) a heart myocardium-coronary vessel interaction causes pressure opposite to $p_{sa}(t)$ with the effect of throttling or even reversing flow; and (iii) the inertial effect of blood accumulated in arteries is negligible.

Based on the foregoing, the CBF component shown generally in FIG. 13 is suitable for determining boundary conditions for CFD simulations of flow in coronary arteries. The CBF component specifies that flow in the coronary artery inlet $q_0(t)$ results from forcing aortic pressure $p_{sa}(t)$ throttled by heart contraction and reverse accumulation, the latter determined mainly by ventricular pressure.

The CBF component describes a causal relationship, with pressure acting as an independent variable. Because pressure serves as the independent variable in the CBF component, the CBF component and its use in patient-specific computational modeling is advantageous over other techniques for determining boundary conditions. Some advantages of using pressure as the independent variable include: (i) pressure is relatively easy to measure when compared to velocity or mass flux, which are much more challenging to measure; and (ii) pressure measurements, even noninvasive and in a location far from heart, will not be vitiated by excessive error.

Figure 14:
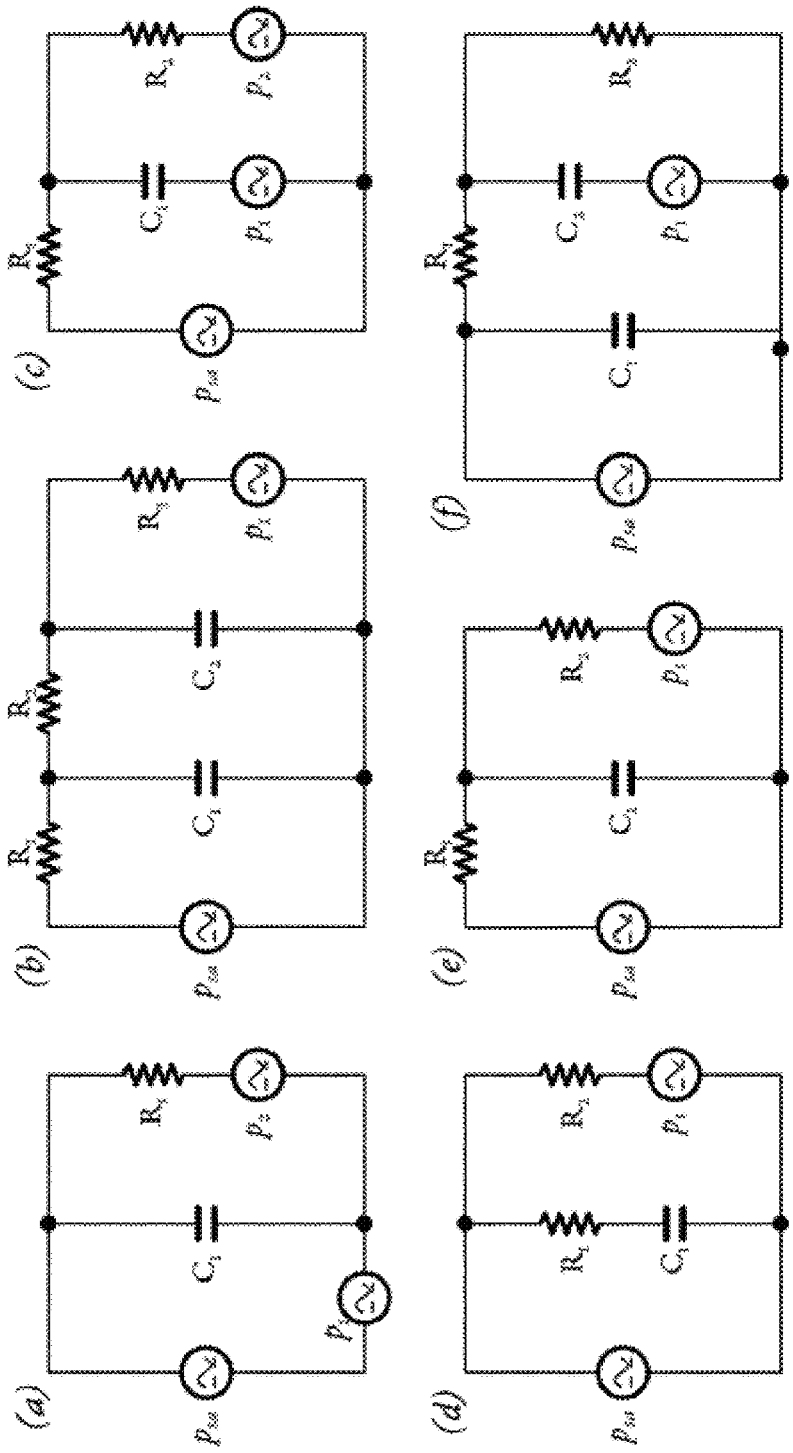
FIG. 14 illustrates six exemplary models suitable for use in a coronary blood flow (CBF) component model.
Figure 15:
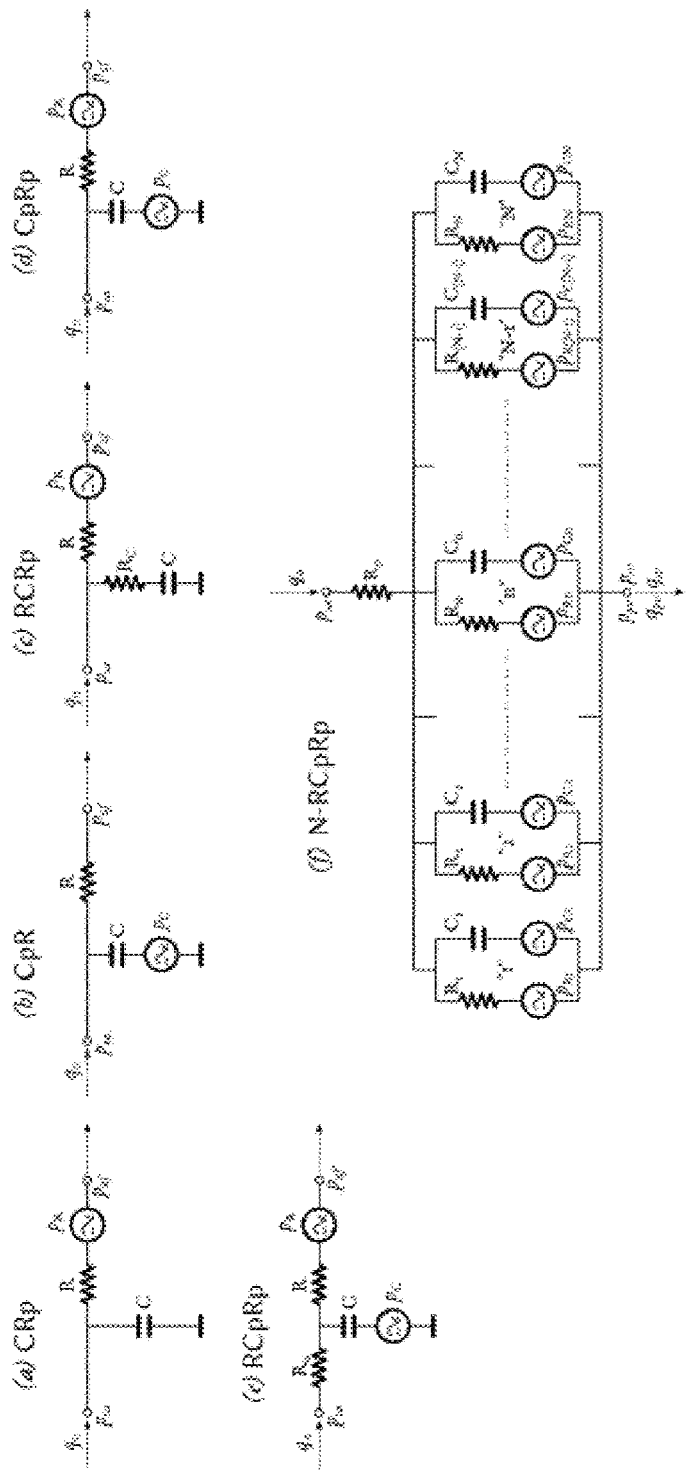
FIG. 15 illustrates five different functional blocks (a)-(e) suitable for use in a multi-compartment coronary blood flow (CBF) model.

Coronary blood flow may be modeled in many different ways (see Beyar R et al. (1987) Time-dependent coronary blood flow distribution in left ventricular wall. American Journal of Physiology, Heart and Circulatory Physiology, Vol. 252, No. 2, Pt. 2, H417-H433; Boileau E et al. (2015) One-Dimensional Modelling of the Coronary Circulation. Application to Noninvasive Quantification of Fractional Flow Reserve (FFR). Computational and Experimental Biomedical Sciences: Methods and Applications, Vol. 21, 137-155; Bruinsma T et al. (1988) Model of the coronary circulation based on pressure dependence of coronary resistance and compliance. Basic Res Cardiol, 83:510-524; Burattini R et al. (1985) Identification of canine intramyocardial compliance on the basis of the waterfall model. Annals of Biomedical Engineering, Vol. 13, No. 5, 385-404; Chadwick R S et al. (1990) Phasic regional myocardial inflow and outflow: comparison of theory and experiments. American Journal of Physiology, Heart and Circulatory Physiology, Vol. 258, No. 6, H1687-H1698; Garcia D et al. (2009) Impairment of coronary flow reserve in aortic stenosis. Journal of Applied Physiology, Vol. 106, No. 1, 113-121; Holenstein R et al. (1990) Parametric analysis of flow in the intramyocardial circulation. Annals of Biomedical Engineering, Vol. 18, No. 4, 347-365; Judd R M et al. (1991) Coronary input impedance is constant during systole and diastole. American Journal of Physiology—Heart and Circulatory Physiology, Vol. 260, No. 6, H1841-H1851; Kresh J Y et al. (1990) Model-based analysis of transmural vessel impedance and myocardial circulation dynamics. American Journal of Physiology, Heart and Circulatory Physiology, Vol. 258, No. 1, H262-H276; Lee J et al. (1984) The role of vascular capacitance in the coronary arteries. Circ Res 55:751-762; Lee J et al. (2012) The multi-scale modelling of coronary blood flow. Annals of Biomedical Engineering, Vol. 40, Issue 11, 2399-2413; Li J K-J (2000) The Arterial Circulation. Physical Principles and Clinical Applications, Springer, New York; Mynard J P et al. (2014) Scalability and in vivo validation of a multiscale numerical model of the left coronary circulation. American Journal of Physiology, Heart and Circulatory Physiology, Vol. 306, No. 4, H517-H528; Marsden A L (2014) Thrombotic risk stratification using computational modeling in patients with coronary artery aneurysms following Kawasaki disease. Biomechanics and Modeling in Mechanobiology, Vol. 13, No. 6, 1261-1276; Spaan J A E et al. (1981) Diastolic-systolic coronary flow differences are caused by intramyocardial pump action in the anesthetized dog. Circ Res, Vol. 49, Issue 3, 584-593, some examples of which are shown in FIG. 14. The coronary blood flow models shown in FIG. 14 may be summarized as follows: (i) all of the models have a single source element, usually assumed to equal aortic pressure ($p_{sa}$) (see id.); (ii) source energy is partially dissipated on one (c,e,f) (see Bruinsma T et al. (1988) Model of the coronary circulation based on pressure dependence of coronary resistance and compliance. Basic Res Cardiol, 83:510-524; Burattini R et al. (1985) Identification of canine intramyocardial compliance on the basis of the waterfall model. Annals of Biomedical Engineering, Vol. 13, No. 5, 385-404; Garcia D et al. (2009) Impairment of coronary flow reserve in aortic stenosis. Journal of Applied Physiology, Vol. 106, No. 1, 113-121; Holenstein R et al. (1990) Parametric analysis of flow in the intramyocardial circulation. Annals of Biomedical Engineering, Vol. 18, No. 4, 347-365; Kresh J Y et al. (1990) Model-based analysis of transmural vessel impedance and myocardial circulation dynamics. American Journal of Physiology, Heart and Circulatory Physiology, Vol. 258, No. 1, H262-H276; Lee J et al. (1984) The role of vascular capacitance in the coronary arteries. Circ Res 55:751-762; Lee J et al. (2012) The multi-scale modelling of coronary blood flow. Annals of Biomedical Engineering, Vol. 40, Issue 11, 2399-2413; Li J K-J (2000) The Arterial Circulation. Physical Principles and Clinical Applications, Springer, New York; Mohrman D et al. (2013) Cardiovascular physiology. McGraw-Hill, Lange, New York; Sengupta D et al.; Spaan J A E et al. (1981) Diastolic-systolic coronary flow differences are caused by intramyocardial pump action in the anesthetized dog. Circ Res, Vol. 49, Issue 3, 584-593.), two (b) (see Chadwick R S et al. (1990) Phasic regional myocardial inflow and outflow: comparison of theory and experiments. American Journal of Physiology, Heart and Circulatory Physiology, Vol. 258, No. 6, H1687-H1698.), or zero (a,d) (see Beyar R et al. (1987) Time-dependent coronary blood flow distribution in left ventricular wall. American Journal of Physiology, Heart and Circulatory Physiology, Vol. 252, No. 2, Pt. 2, H417-H433; Boileau E et al. (2015) One-Dimensional Modelling of the Coronary Circulation. Application to Noninvasive Quantification of Fractional Flow Reserve (FFR). Computational and Experimental Biomedical Sciences: Methods and Applications, Vol. 21, 137-155; Garcia D et al. (2009) Impairment of coronary flow reserve in aortic stenosis. Journal of Applied Physiology, Vol. 106, No. 1, 113-121; Judd R M et al. (1991) Coronary input impedance is constant during systole and diastole. American Journal of Physiology—Heart and Circulatory Physiology, Vol. 260, No. 6, H1841-H1851; Li J K-J (2000) The Arterial Circulation. Physical Principles and Clinical Applications, Springer, New York; Mynard J P et al. (2014) Scalability and in vivo validation of a multiscale numerical model of the left coronary circulation. American Journal of Physiology, Heart and Circulatory Physiology, Vol. 306, No. 4, H517-H528.) resistive elements; (iii) inflow is typically divided between a singular resistive and capacitive branch, with a few models having two capacitive elements (b,f) (see Burattini R et al. (1985) Identification of canine intramyocardial compliance on the basis of the waterfall model. Annals of Biomedical Engineering, Vol. 13, No. 5, 385-404; Chadwick R S et al. (1990) Phasic regional myocardial inflow and outflow: comparison of theory and experiments. American Journal of Physiology, Heart and Circulatory Physiology, Vol. 258, No. 6, H1687-H1698; Li J K-J (2000) The Arterial Circulation. Physical Principles and Clinical Applications, Springer, New York; Marsden A L (2014) Thrombotic risk stratification using computational modeling in patients with coronary artery aneurysms following Kawasaki disease. Biomechanics and Modeling in Mechanobiology, Vol. 13, No. 6, 1261-1276; Sengupta D et al.); (iv) the capacitive branch may include its own resistive element (d) (see Garcia D et al. (2009) Impairment of coronary flow reserve in aortic stenosis. Journal of Applied Physiology, Vol. 106, No. 1, 113-121; Judd R M et al. (1991) Coronary input impedance is constant during systole and diastole. American Journal of Physiology—Heart and Circulatory Physiology, Vol. 260, No. 6, H1841-H1851; Li J K-J (2000) The Arterial Circulation. Physical Principles and Clinical Applications, Springer, New York.) or source as a function of intraventricular pressure (c,f) (see Burattini R et al. (1985) Identification of canine intramyocardial compliance on the basis of the waterfall model. Annals of Biomedical Engineering, Vol. 13, No. 5, 385-404; Garcia D et al. (2009) Impairment of coronary flow reserve in aortic stenosis. Journal of Applied Physiology, Vol. 106, No. 1, 113-121; Kresh J Y et al. (1990) Model-based analysis of transmural vessel impedance and myocardial circulation dynamics. American Journal of Physiology, Heart and Circulatory Physiology, Vol. 258, No. 1, H262-H276; Lee J et al. (2012) The multi-scale modelling of coronary blood flow. Annals of Biomedical Engineering, Vol. 40, Issue 11, 2399-2413; Li J K-J (2000) The Arterial Circulation. Physical Principles and Clinical Applications, Springer, New York; Sengupta D et al.; Spaan J A E et al. (1981) Diastolic-systolic coronary flow differences are caused by intramyocardial pump action in the anesthetized dog. Circ Res, Vol. 49, Issue 3, 584-593.), but not both; (v) the resistive branch usually includes its own source related to intraventricular pressure (a,b,c,d,e) (see Beyar R et al. (1987) Time-dependent coronary blood flow distribution in left ventricular wall. American Journal of Physiology, Heart and Circulatory Physiology, Vol. 252, No. 2, Pt. 2, H417-H433; Boileau E et al. (2015) One-Dimensional Modelling of the Coronary Circulation. Application to Noninvasive Quantification of Fractional Flow Reserve (FFR). Computational and Experimental Biomedical Sciences: Methods and Applications, Vol. 21, 137-155; Bruinsma T et al. (1988) Model of the coronary circulation based on pressure dependence of coronary resistance and compliance. Basic Res Cardiol, 83:510-524; Chadwick R S et al. (1990) Phasic regional myocardial inflow and outflow: comparison of theory and experiments. American Journal of Physiology, Heart and Circulatory Physiology, Vol. 258, No. 6, H1687-H1698; Garcia D et al. (2009) Impairment of coronary flow reserve in aortic stenosis. Journal of Applied Physiology, Vol. 106, No. 1, 113-121; Holenstein R et al. (1990) Parametric analysis of flow in the intramyocardial circulation. Annals of Biomedical Engineering, Vol. 18, No. 4, 347-365; Judd R M et al. (1991) Coronary input impedance is constant during systole and diastole. American Journal of Physiology—Heart and Circulatory Physiology, Vol. 260, No. 6, H1841-H1851; Kresh J Y et al. (1990) Model-based analysis of transmural vessel impedance and myocardial circulation dynamics. American Journal of Physiology, Heart and Circulatory Physiology, Vol. 258, No. 1, H262-H276; Lee J et al. (1984) The role of vascular capacitance in the coronary arteries. Circ Res 55:751-762; Lee J et al. (2012) The multi-scale modelling of coronary blood flow. Annals of Biomedical Engineering, Vol. 40, Issue 11, 2399-2413; Li J K-J (2000) The Arterial Circulation. Physical Principles and Clinical Applications, Springer, New York; Mynard J P et al. (2014) Scalability and in vivo validation of a multiscale numerical model of the left coronary circulation. American Journal of Physiology, Heart and Circulatory Physiology, Vol. 306, No. 4, H517-H528; Spaan J A E et al. (1981) Diastolic-systolic coronary flow differences are caused by intramyocardial pump action in the anesthetized dog. Circ Res, Vol. 49, Issue 3, 584-593.). In general, these can be considered as multi-compartment models built on functional blocks shown in FIG. 15.

Figure 16:
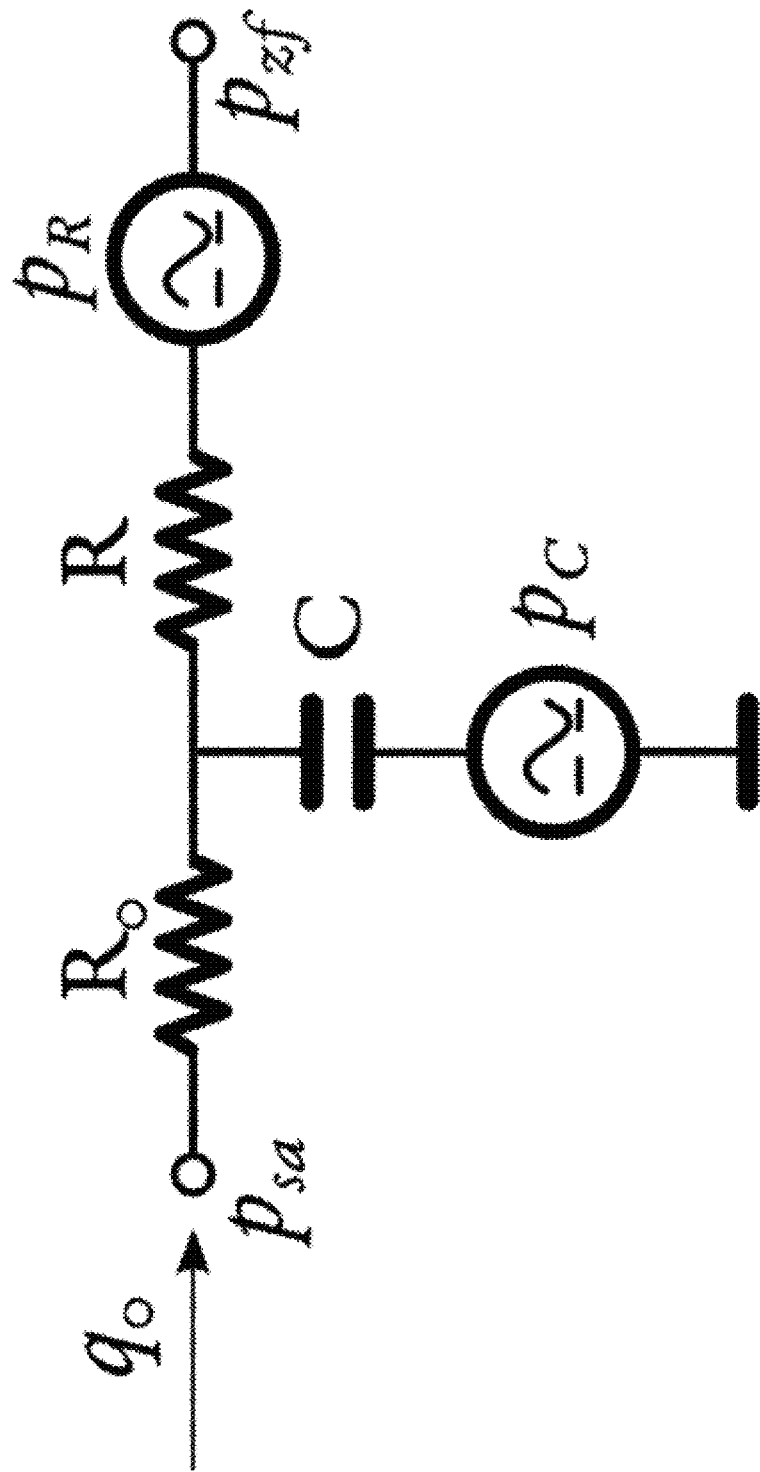
FIG. 16 illustrates a set of parameters of a functional block suitable for use in a coronary blood flow (CBF) component model.

In a preferred embodiment, coronary blood flow is modeled using the lumped functional block shown in FIG. 16. Use of the coronary blood flow model shown in FIG. 16 may require solving the following mass flux conservation equation:

$$R_0 C \frac{dq_0}{dt} + q_0 = C \frac{d(p_{sa} - p_c)}{dt} + \frac{(p_{sa} - p_R - p_{zf})}{R} H(p_{sa} - p_R - p_{zf}),$$

where H is the Heaviside step function. The throttling pressure $p_R$ as well as $p_C$ describes myocardium-coronary vessel interaction (MVI), wherein $p_C = k_C \cdot (CEP+SIP)$ and $p_R = k_R(CEP+SIP)$ (see Boileau E et al. (2015) One-Dimensional Modelling of the Coronary Circulation. Application to Noninvasive Quantification of Fractional Flow Reserve (FFR). Computational and Experimental Biomedical Sciences: Methods and Applications, Vol. 21, 137-155; Bruinsma T et al. (1988) Model of the coronary circulation based on pressure dependence of coronary resistance and compliance. Basic Res Cardiol, 83:510-524; Epstein S et al. (2015) Reducing the number of parameters in 1D arterial blood flow modeling: less is more for patient-specific simulations. American Journal of Physiology, Heart and Circulatory Physiology, Vol. 309, No. 1, H222-H234; Mohrman D et al. (2013) Cardiovascular physiology. McGraw-Hill, Lange, New York; Pappano A et al. (2013) Cardiovascular physiology. Elsevier; Zamir M (2005) The physics of coronary blood flow. Springer-Verlag.). There are three main hypotheses of the passive interaction mechanism, and the extravascular pressure description can include (see Algranati D et al. (2010) Mechanisms of myocardium-coronary vessel interaction. American Journal of Physiology. Heart and Circulatory Physiology, Vol. 298, No. 3, H861-H873; Mynard J P et al. (2014) Scalability and in vivo validation of a multiscale numerical model of the left coronary circulation. American Journal of Physiology. Heart and Circulatory Physiology, Vol. 306, No. 4, H517-H528; Westerhof N et al. (2006) Cross-talk between cardiac muscle and coronary vasculature. Physiological Reviews, Vol. 86, No. 4, 1263-1308): (i) interstitial, cavity-induced extracellular pressure (CEP=$\mu_1 \cdot p_V$), and (ii) shortening-induced intracellular pressure (SIP=$\mu_2 \cdot E_V$). The instantaneous heart left (or right, respectively) ventricle pressure $p_V$ and elastance $E_V$ may be taken from the HPV component and the zero flow pressure $p_{zf}$ may be assumed to equal 20 mmHg or less.

Figure 17:
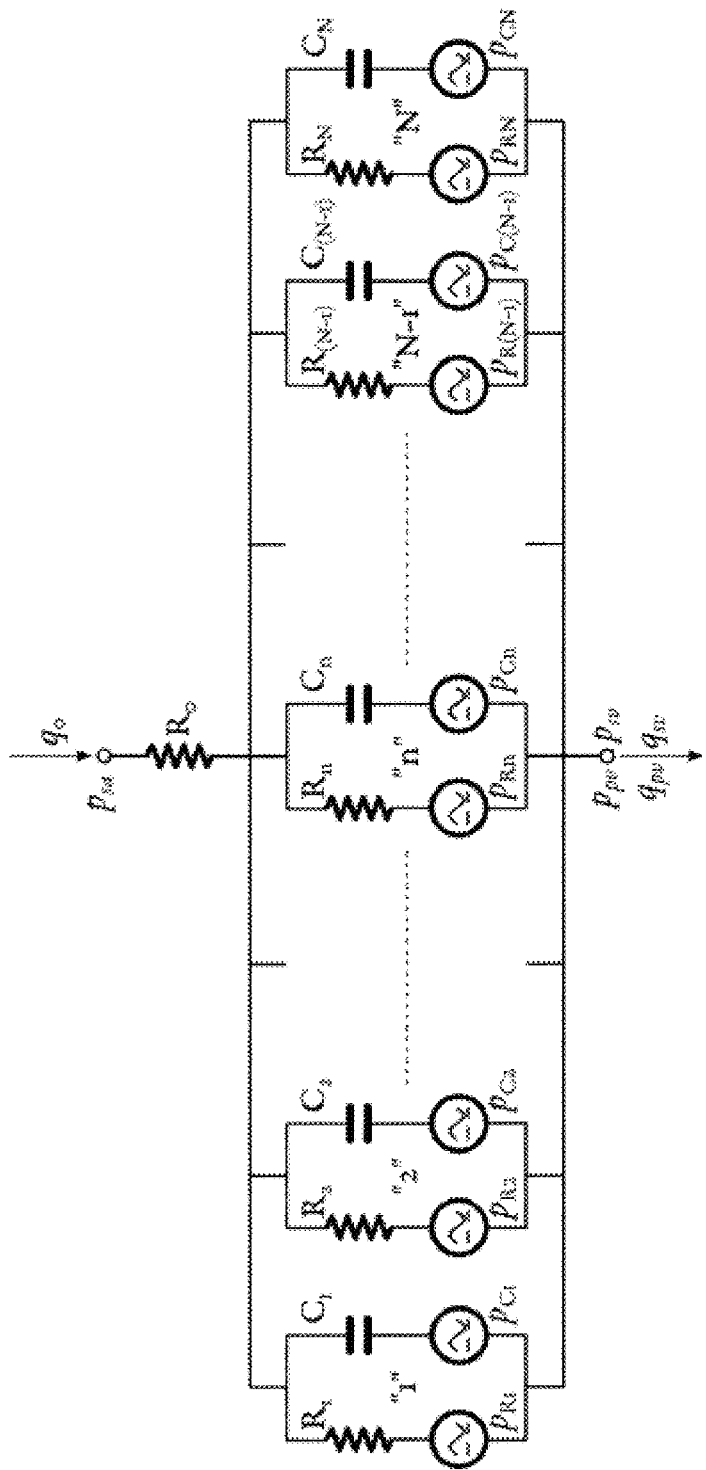
FIG. 17 illustrates a lumped parameter multilayer/multi-compartment model with describing parameters, suitable for use in a coronary blood flow (CBF) component model.

Coronary arteries are spatially distributed in the heart wall and affected by extracellular pressure in a non-uniform manner, and they may be additionally moderated by physical or pharmacological stress conditions—especially hyperemia by administration of adenosine receptors (purinergic P1 receptors) agonists such as Adenocard or Adenoscan or more selective agonist of A2A receptor (Regadenoson, Binodenoson). In embodiments, the effect of heart wall heterogeneity (modified additionally under the influence of stress) may be described by utilizing a multilayer and multicompartment model with a variable tissue pressure coefficient (see Garcia D et al. (2009) Impairment of coronary flow reserve in aortic stenosis. Journal of Applied Physiology, Vol. 106, No. 1, 113-121; Holenstein R et al. (1990) Parametric analysis of flow in the intramyocardial circulation. Annals of Biomedical Engineering, Vol. 18, No. 4, 347-365; Westerhof N et al. (2006) Cross-talk between cardiac muscle and coronary vasculature. Physiological Reviews, Vol. 86, No. 4, 1263-1308.), an example of which is shown in FIG. 17. According to FIG. 17:

$$\sum_{n=1}^{N} R_0 C_n \frac{dq_n}{dt} + \sum_{n=1}^{N} q_n = \sum_{n=1}^{N} C_n \frac{d}{dt}(p_{sa} - K_p(n)k_C(CEP + SIP)) +$$

$$\sum_{n=1}^{N} \frac{p_{sa} - K_p(n)k_R(CEP + SIP) - p_{zf}}{R_n} H(p_{sa} - K_p(n)k_R(CEP + SIP) - p_{zf})$$

where the heart tissue pressure coefficient is:

$$K_p(n) = \left(\frac{2n-1}{2N}\right)^k$$

During resting condition, extravascular pressure decreases nonlinearly, concave downward from endocardium to epicardium with exponent $k \approx 2.0$ or greater. Contrary to this, at the cassation of any active coronary vasomotor tone (hypothetical maximum coronary dilation) the linear relationship can be assumed ($k \approx 1.0$).

The vasodilating effect related to elimination of active coronary vasomotor tone may not be limited to heart tissue and function. More generally, vasodilation is just one of the cardiac tropism form (chronotropism, inotropism, lusitropism, and many others). Furthermore, endogenous and/or exogenous mediators may cause a decrease in vascular resistance and allow an increase in coronary blood flow—as well as—systemic and pulmonary blood flow. In a preferred embodiment, net cardiac tropism effects ($E/E_{max}$) of purinergic receptor (R) binding endo- or exogenous agonists (A) may be modeled by the cooperative kinetics relation $$\frac{E}{E_{max}} = \frac{[AR]^n}{K_E^n + [AR]^n}$$

where concentration of occupied receptors $$[AR] = \frac{[R_0][A]}{K_A + [A]}$$

Combining these equations and introduction transducer ratio $\tau = [R_0]/K_E$, we get explicit relation $$\frac{E}{E_{max}} = \frac{\tau^n [A]^n}{(K_A + [A])^n + \tau^n [A]^n}$$

cooperative purinergic receptor-stimulus model of agonism (using affinities $K_A$, and efficacies $K_E$).

In step 110, a computer system may simulate blood flow in the patient-specific anatomical model (e.g., the coronary arteries) using CFD and the patient-specific boundary conditions. In particular, the CFD simulation may use the coronary volumetric flow rate waveform at the inlets and/or outlets of the coronary arteries, which may be determined at least in part by patient-specific continuous arterial pressure data, as boundary conditions for the CFD modeling.

Figure 19:
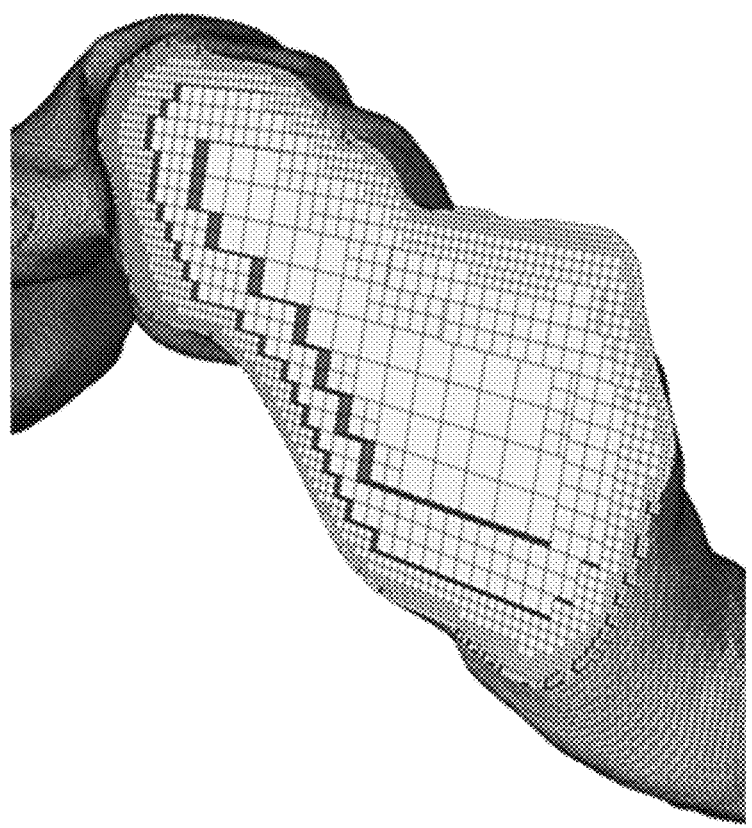
FIG. 19 is an example 3D mesh of a portion of a patient's blood vessel.

Prior to running the CFD simulation, a 3D mesh may be created for the patient specific anatomical model, together with separate inflow and outflow boundary models, to enable the CFD simulation (e.g., create a 3D computational grid for numerical simulations). The 3D mesh may include a plurality of nodes (e.g., meshpoints or gridpoints) along the surfaces of the patient-specific anatomical model and throughout the interior of the patient-specific anatomical model (see FIG. 19). The generated mesh may be reviewed and/or corrected by the computer system and/or the user, if necessary (e.g., to correct mesh distortions, insufficient spatial resolution in the mesh, etc.).

In the CFD simulation, blood may be modeled as a Newtonian fluid or a non-Newtonian fluid, and the flow fields may be obtained by numerically solving the discretized mass and momentum (Navier-Stokes) balance equations under the rigid wall assumption. Numerical methods to solve the three-dimensional equations of blood flow may include finite difference, finite volume, spectral, lattice Boltzmann, particle-based, level set, isogeometric, or finite element methods, or other computational fluid dynamics (CFD) numerical techniques. The discretized Navier-Stokes equations may be used to incrementally simulate velocity of blood flow and pressure within the coronary arteries over time. That is, the CFD simulation may determine blood flow and pressure at each of the nodes of the meshed anatomical model. The result of the CFD simulations may be patient-specific blood flow and pressure distribution in the patient's coronary arteries based on patient-specific anatomy and patient-specific boundary conditions.

In step 112, a computer system may determine one or more hemodynamic parameters associated with the patient's coronary arteries. The one or more hemodynamic parameters may be determined based at least in part on the CFD simulation results. Examples of hemodynamic parameters may include coronary artery characteristics such as blood pressure, blood flow rate, wall shear stress (WSS), oscillatory shear index (OSI), relative residence time (RRT), fractional flow reserve (FFR), coronary flow reserve (CFR), instantaneous wave-free ratio (iFR), and the like. The hemodynamic parameters may be interpolated across the patient-specific anatomical model to provide a user with information about the hemodynamic parameters across the anatomical model.

In step 114, a computer system may output the one or more determined hemodynamic parameters. The computer system may, for example, display the one or more hemodynamic parameters or visualizations (e.g., 2D or 3D images) of the one or more hemodynamic parameters. The computer system may, for example, present the hemodynamic parameters as a three-dimensional interactive visualization. The computer system may send the one or more determined hemodynamic parameters to a remote computer for display on the remote computer.

In step 116, the one or more determined hemodynamic parameters are used to determine and/or as part of a patient-specific treatment plan. In an embodiment, the one or more determined hemodynamic parameters are used to plan a coronary revascularization procedure in cardiovascular disease. For example, the one or more determined hemodynamic parameters may be used to determine an optimal, patient-specific location for stent placement in a patient that improves hemodynamic conditions for blood flow in the patient's coronary arteries, and then the stent is positioned at the determined optimal location. As another example, the one or more determined hemodynamic parameters may be used to determine an optimal coronary artery bypass procedure in a patient that provides better hemodynamic conditions for coronary artery flow in the patient when compared to alternative coronary artery bypass procedures, and then a physician performs the optimal coronary artery bypass procedure in the patient.

In an embodiment, the one or more determined hemodynamic parameters are used in support of a virtual cardiopulmonary exercise test. For example, the one or more determined hemodynamic parameters may include a fractional flow reserve (FFR) estimation, which can be used to provide a non-invasive estimation of fractional flow reserve and/or oxygen blood saturation during virtual cardiopulmonary exercise test conditions.

Although the above embodiments have been described in reference to a transient simulation of blood flow through coronary arteries, it is understood that the present disclosure also encompasses steady-state simulation of blood flow through coronary arteries.

Blood flow through the coronary arteries is pulsatile. Its pressure and velocity are changing in time during a single heart beat and this process is repetitive. The most straightforward way of simulating such a flow is to use a transient solver, but this may be very time consuming. Use of a steady-state (e.g., stationary) simulation may be advantageous as its time-to-solution is relatively shorter but it is not applicable to every non-stationary phenomena.

To take advantage of a stationary simulation, coronary arteries may be treated as a pipeline system. In such a system, the pressure drop $\Delta p$ is dependent on fluid velocity v. For a general flow, the pressure drop is a quadratic function of velocity ($\Delta p = av^2 + bv + c$). To determine the coefficients in this equation, one needs to find three pairs of (v, $\Delta p$) values. To do this, three steady-state simulations can be run for various pressure and velocity (calculated from flow rate) value boundary conditions and the pressure drop values respective to those velocities can be found. As those simulations are independent, they may be run in parallel. This allows for a great reduction of time-to-solution. For example, results of a transient simulation which take tens of hours to complete may be obtained from a stationary simulation in less than an hour. To take into the account the inertia effect, an additional term was added to the equation for the pressure drop (see Bird R B et al. (1960) Transport Phenomena. John Wiley & Sons, New York; Young D et al. (1973) Flow characteristics in models of arterial stenoses. II. Unsteady flow, Journal of Biomechanics, Vol. 6, No. 5, 547-559; Young D et al. (1977) Hemodynamics of arterial stenoses at elevated flow rates. Circulation Research, Vol. 41, No. 1, 99-107.):

$$\Delta p = av^2 + bv + c + kl\frac{dv}{dt}$$

where: a, b, c—coefficients calculated based on stationary simulations, k=1.2—inertia coefficient, l—distance from inlet.

FIGS. 21-24 show low-detail or high detail schematic block diagrams of a method for patient-specific modeling of hemodynamic parameters in coronary arteries using a steady-state simulation or a transient simulation. As shown in FIGS. 21-24, there are a few differences between a steady-state simulation based method and a transient simulation based method. However, many of the implementation details for a steady-state simulation based method can be applied to a transient simulation based method, and vice versa.

Figure 21:
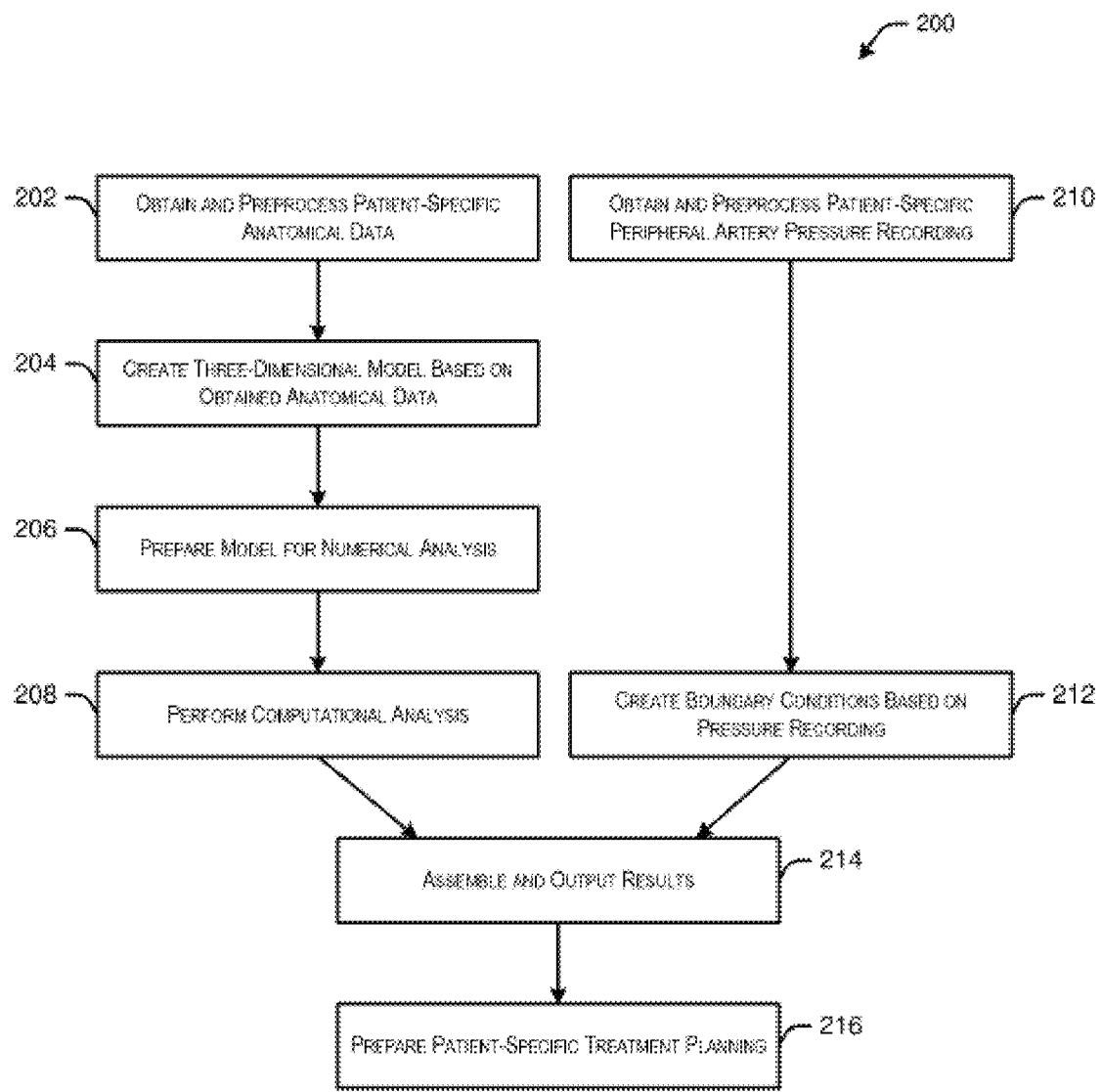
FIG. 21 is a schematic block diagram of a method for patient-specific modeling of hemodynamic parameters in coronary arteries using a steady-state simulation in accordance with one or more example embodiments of the disclosure.
Figure 22:
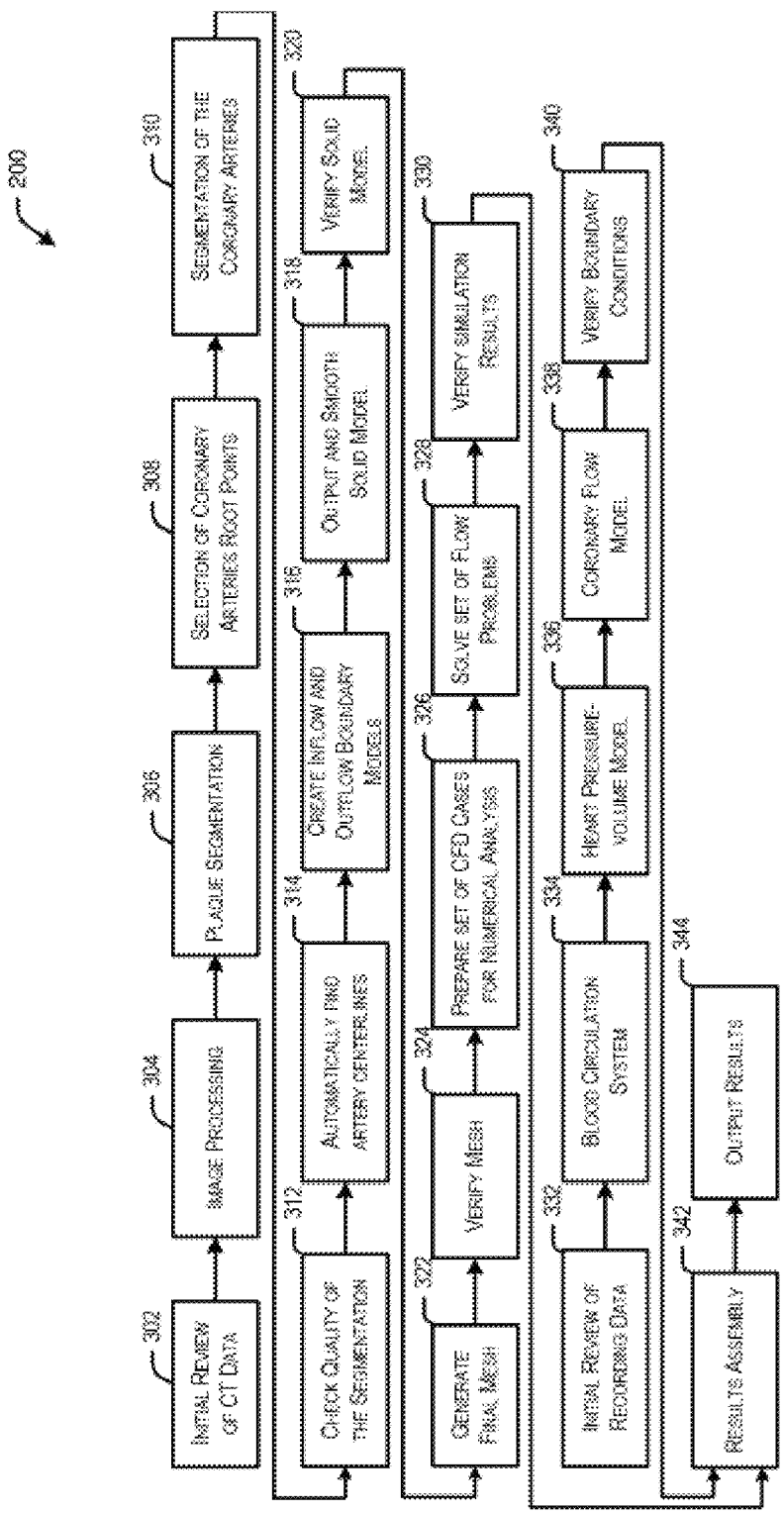
FIG. 22 is a schematic block diagram of a method for patient-specific modeling of hemodynamic parameters in coronary arteries using a steady-state simulation in accordance with one or more example embodiments of the disclosure.

In reference to FIGS. 21-22, shown are a low-detail or high detail schematic block diagram of a method 200 for patient-specific modeling of hemodynamic parameters in coronary arteries using a steady-state simulation.

With specific reference to FIG. 21, in step 202, patient-specific anatomical data is obtained and pre-processed. In step 204, a three-dimensional model is created based on the obtained anatomical data. In step 206, the three-dimensional model is prepared for numerical analysis. In step 208, a computational analysis is performed using the three-dimensional model. In step 210, patient-specific peripheral artery pressure recording data is obtained and preprocessed. In step 212, boundary conditions are created based on the pressure recording data. In step 214, the results of the computational analysis and boundary conditions are assembled and output. In step 216, a patient-specific treatment plan is prepared based on the results.

With specific reference to FIG. 22, in step 302, acquired patient-specific anatomical data (e.g., CT data) is initially reviewed. In step 304, the acquired anatomical data undergoes image processing. In step 306, which marks the beginning of creating a three-dimensional model from the obtained anatomical data, plaque is segmented. In step 308, coronary artery root points are selected. In step 310, the coronary arteries are segmented. In step 312, the quality of the segmentation is checked. In step 314, the artery centerlines are automatically found. In step 316, inflow and outflow boundary models are created. In step 318, the solid model is output and smoothed. In step 320, the output solid model is verified. In step 322, which marks the beginning of preparing the solid model for numerical analysis, a final mesh of the model is generated. In step 324, the mesh is verified. In step 326, which marks the beginning of performing the computational analysis, a set of CFD cases is prepared for numerical analysis. In step 328, the set of CFD cases is solved by flow simulations. In step 330, the simulation results are verified. In step 332, acquired patient-specific anatomical data (e.g., recorded pressure data) is initially reviewed. In step 334, which begins the creation of boundary conditions based on the recorded pressure data, pressure data is input to a blood circulation system model. In step 336, results from the blood circulation system model are input into a heart chambers model. In step 338, results from the heart chambers model are input into a coronary blood flow model, the outputs of which are used to determine boundary conditions. In step 340, the results of the boundary condition determination are verified. In step 342, the results of the boundary condition determination and computational fluid dynamics analysis are assembled. In step 344, the assembled results are output.

Figure 23:
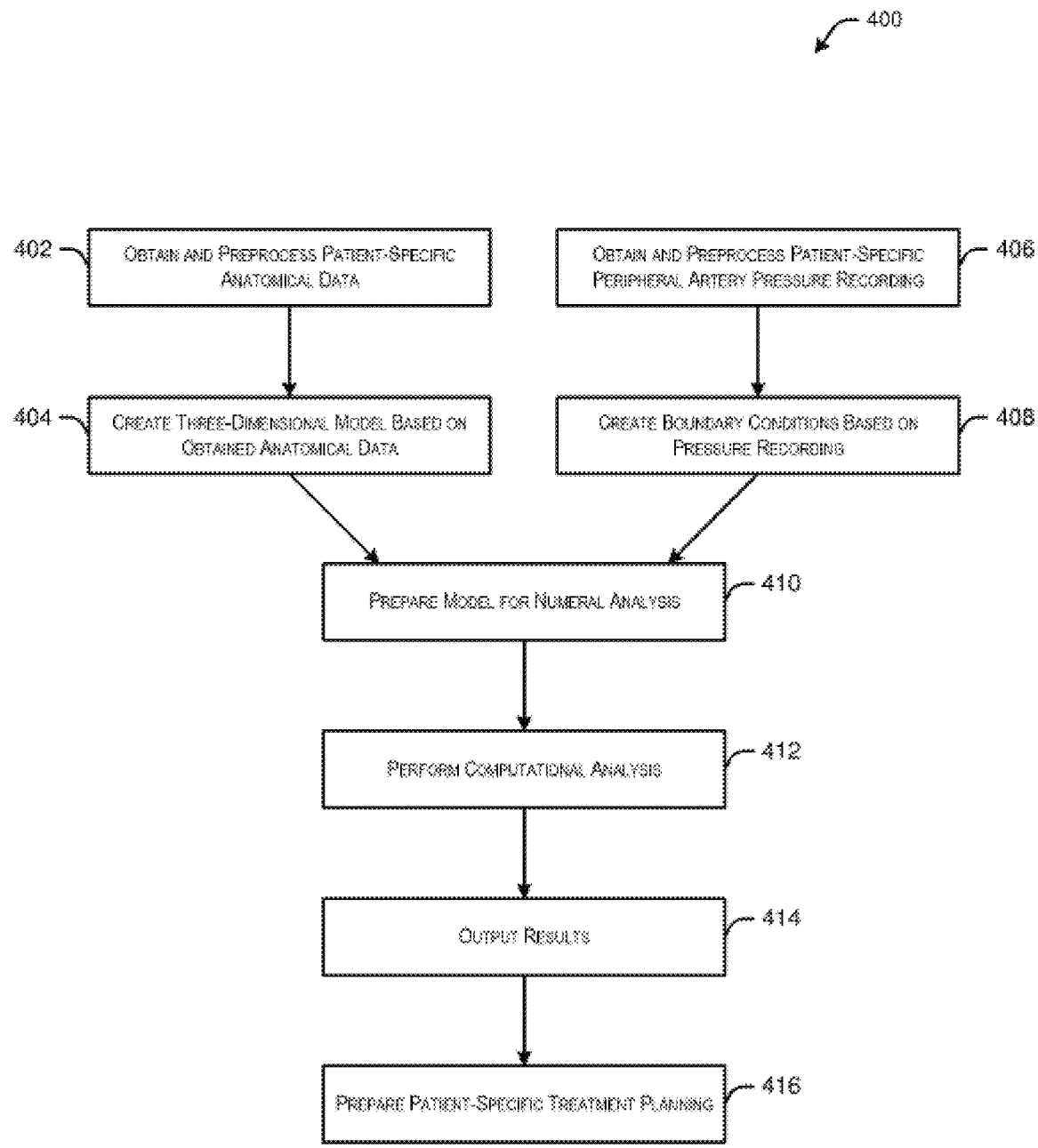
FIG. 23 is a schematic block diagram of a method for patient-specific modeling of hemodynamic parameters in coronary arteries using a transient simulation in accordance with one or more example embodiments of the disclosure.
Figure 24:
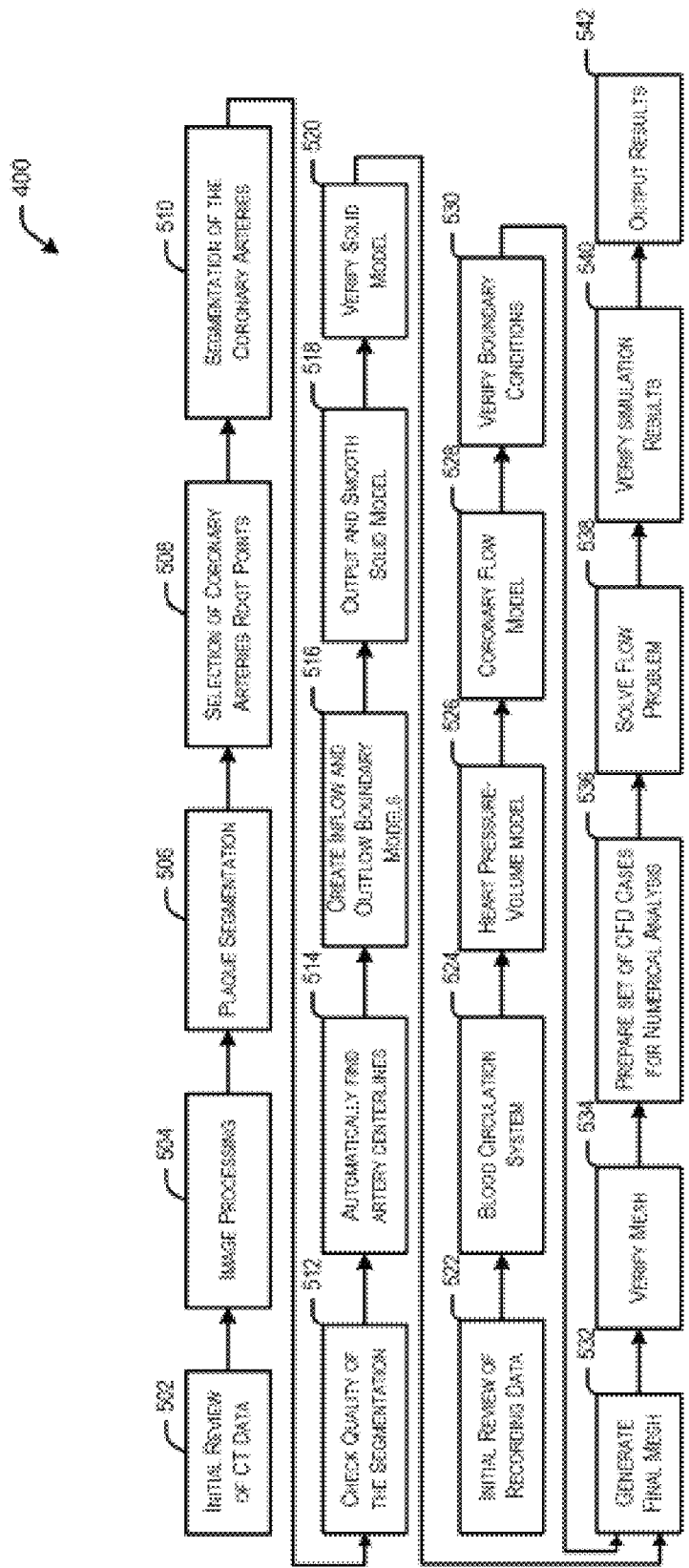
FIG. 24 is a schematic block diagram of a method for patient-specific modeling of hemodynamic parameters in coronary arteries using a transient simulation in accordance with one or more example embodiments of the disclosure.

In reference to FIGS. 23-24, shown are a low-detail or high detail schematic block diagrams of a method 400 for patient-specific modeling of hemodynamic parameters in coronary arteries using a transient simulation.

With specific reference to FIG. 23, in step 402, patient-specific anatomical data is obtained and pre-processed. In step 404, a three-dimensional model is created based on the obtained anatomical data. In step 406, patient-specific peripheral artery pressure recording data is obtained and preprocessed. In step 408, boundary conditions are created based on the pressure recording data. In step 410, the three-dimensional model is prepared for numerical analysis. In step 412, a computational analysis is performed using the three-dimensional model and boundary conditions. In step 414, the results of the computational analysis are output. In step 416, a patient-specific treatment plan is prepared based on the results.

With specific reference to FIG. 24, in step 502, acquired patient-specific anatomical data (e.g., CT data) is initially reviewed. In step 504, the acquired anatomical data undergoes image processing. In step 506, which marks the beginning of creating a three-dimensional model from the obtained anatomical data, plaque is segmented. In step 508, coronary artery root points are selected. In step 510, the coronary arteries are segmented. In step 512, the quality of the segmentation is checked. In step 514, the artery centerlines are automatically found. In step 516, inflow and outflow boundary models are created. In step 518, the solid model is output and smoothed. In step 520, the output solid model is verified. In step 522, acquired patient-specific anatomical data (e.g., recorded pressure data) is initially reviewed. In step 524, which begins the creation of boundary conditions based on the recorded pressure data, pressure data is input to a blood circulation system model. In step 526, results from the blood circulation system model are input into a heart chambers model. In step 528, results from the heart chambers model are input into a coronary blood flow model, the outputs of which are used to determine boundary conditions. In step 530, the results of the boundary condition determination are verified. In step 532, which marks the beginning of preparing the solid model for numerical analysis, a final mesh of the model is generated. In step 534, the mesh is verified. In step 536, which marks the beginning of performing the computational analysis, a CFD case is prepared for numerical analysis. In step 538, the CFD case is solved by flow simulation. In step 540, the simulation results are verified. In step 542, the results are output.

Although embodiments have been described in language specific to structural features and/or methodological acts, it is to be understood that the disclosure is not necessarily limited to the specific features or acts described. Rather, the specific features and acts are disclosed as illustrative forms of implementing the embodiments. Conditional language, such as, among others, "can," "could," "might," or "may," unless specifically stated otherwise, or otherwise understood within the context as used, is generally intended to convey that certain embodiments could include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment. Publications cited herein and the materials for which they are cited are specifically incorporated by reference.

EXAMPLES

Example 1

Figure 25:
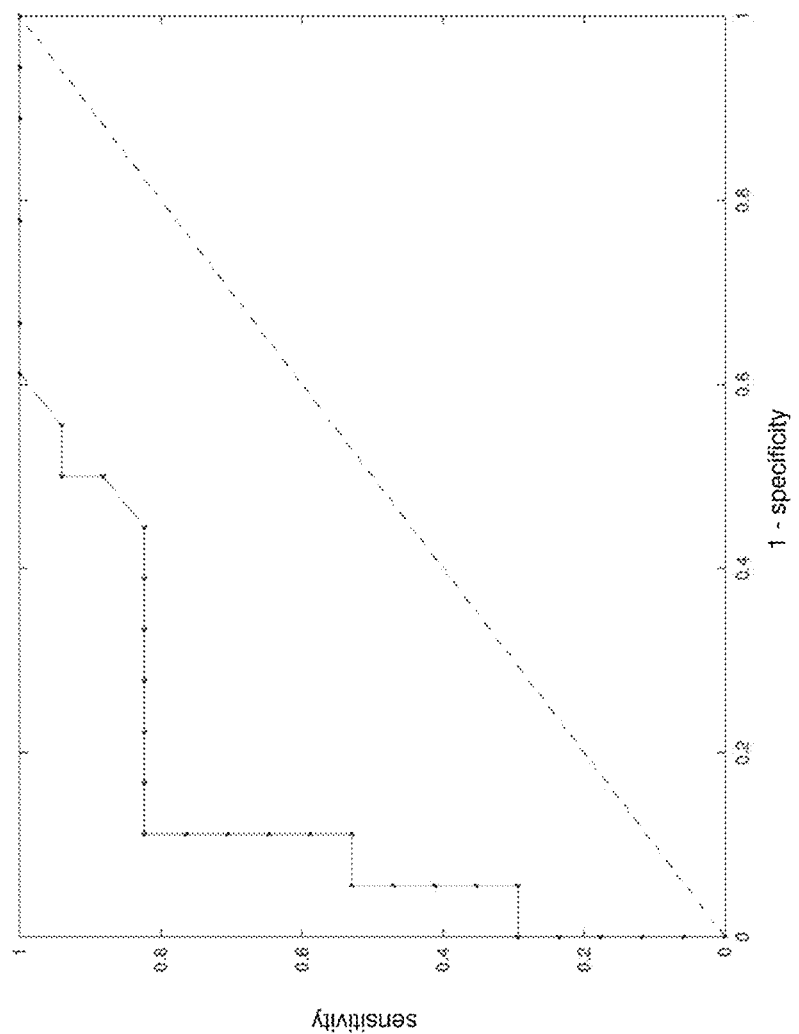
FIG. 25 is a receiver operating characteristic (ROC) curve comparing fractional flow reserve (FFR) results obtained using a three-component model variant to real-life results.

Results from a method for patient-specific modeling of hemodynamic parameters in coronary arteries in accordance with one or more example embodiments of the disclosure were compared to real life results. In particular, invasively collected FFR data from 30 patients in 3 hospitals was compared to numerically calculated FFR values using one or more example embodiments of the disclosure. The statistical results for a total of 35 stenoses are summarized in the table below and in FIG. 25.

| | |
|---|---|
| Sensitivity | 82.4% |
| Specificity | 88.9% |
| Positive Predictive Value | 87.5% |
| Negative Predictive Value | 84.2% |
| Accuracy | 85.7% |
| Area under ROC curve | 0.863 |

The invention claimed is:
1. A method of generating a coronary artery model comprising:
receiving patient-specific anatomical structure data and patient-specific physiological data, wherein the anatomical structure data comprises structural information about a patient's coronary arteries, and wherein the patient-specific physiological data comprises a continuously recorded blood pressure waveform from a non-invasive measurement;

generating, based at least in part on the anatomical structure data, an anatomical model of at least a portion of the patient's coronary arteries;

generating an inflow or an outflow waveform boundary condition for a computational fluid dynamics (CFD) simulation of blood flow in the anatomical model by:
(i) assigning the continuously recorded blood pressure waveform as the boundary condition, and
(ii) using the continuously recorded blood pressure waveform to model the boundary condition;

simulating blood flow in the anatomical model using CFD and the inflow or the outflow waveform boundary condition for the CFD simulation of blood flow; and determining, based at least in part on the simulation, one or more hemodynamic parameters associated with the patient's coronary arteries, thereby generating a coronary artery model.

2. The method of claim 1, wherein the anatomical structure data is from a non-invasive measurement.

3. The method of claim 1, wherein the anatomical structure data is from a computed tomography angiogram.

4. The method of claim 1, wherein generating the anatomical model does not include segmenting an aorta.

5. The method of claim 1, wherein the anatomical model is a model of only the patient's coronary arteries.

6. The method of claim 1, wherein the inflow or the outflow waveform boundary condition comprises an inflow boundary condition for the patient's coronary arteries or an outflow boundary condition for the patient's coronary arteries.

7. The method of claim 1, wherein generating the inflow or the outflow waveform boundary condition comprises:
determining, based at least in part on a blood circulation system model and the continuously recorded blood pressure waveform, volumetric blood flow rate data;
determining, based at least in part on a heart chambers pressure-volume model and the volumetric blood flow rate data, ventricle pressure data;
determining, based at least in part on a coronary blood flow model, the continuously recorded blood pressure waveform, and the ventricle pressure data, coronary artery inlet flow data.

8. The method of claim 7, wherein generating the inflow or the outflow waveform boundary condition comprises determining, based at least in part on an allometric scaling law and the coronary artery inlet flow data, coronary artery outlet flow data.

9. The method of claim 7, wherein the heart chambers pressure-volume model is a time-varying elastance model.

10. The method of claim 1, wherein the blood flow simulations are carried out using a transient solver or a steady-state solver.

11. The method of claim 1, wherein the CFD simulation comprises determining vessel flow and pressure drop characteristics with a steady-state approach.

12. The method of claim 1, wherein the one or more hemodynamic parameters are selected from blood pressure, blood flow, blood flow rate, wall shear stress (WSS), oscillatory shear index (OSI), relative residence time (RRT), fractional flow reserve (FFR), instantaneous wave-free ration (iFR), and coronary flow reserve (CFR).

13. The method of claim 1, further comprising outputting the one or more determined hemodynamic parameters.

14. The method of claim 13, wherein the outputting comprises sending the one or more determined hemodynamic parameters to a display device.

15. The method of claim 13, wherein the outputting comprises sending the one or more determined hemodynamic parameters to a remote computer.

16. The method of claim 13, further comprising determining a patient-specific treatment plan based, at least in part, on the one or more determined hemodynamic parameters.

17. The method of claim 16, wherein the patient-specific treatment plan is an optimal, patient-specific location for stent placement in the patient.

18. The method of claim 1, wherein the continuously recorded blood pressure waveform is a continuous waveform.

19. The method of claim 1, wherein (i) and (ii) are performed in sequence.

20. The method of claim 1, further comprising modeling overall blood circulation in the patient using a multi-compartment model comprising the anatomical model of the patient's coronary arteries or a portion thereof and a systemic and/or pulmonary circulation model.

* * * * *